US012809256B2

(12) United States Patent
Sakano et al.

(10) Patent No.: US 12,809,256 B2
(45) Date of Patent: Nov. 24, 2026

(54) RADIATION-SENSITIVE RESIN COMPOSITION, METHOD FOR FORMING RESIST PATTERN, POLYMER, AND COMPOUND

(71) Applicant: JSR CORPORATION, Tokyo (JP)

(72) Inventors: Nozomi Sakano, Tokyo (JP); Ryuichi Nemoto, Tokyo (JP)

(73) Assignee: JSR CORPORATION, Tokyo (JP)

( * ) Notice: Subject to any disclaimer, the term of this patent is extended or adjusted under 35 U.S.C. 154(b) by 621 days.

(21) Appl. No.: 18/235,420

(22) Filed: Aug. 18, 2023

(65) Prior Publication Data

US 2023/0393469 A1 Dec. 7, 2023

Related U.S. Application Data

(63) Continuation-in-part of application No. PCT/JP2022/007670, filed on Feb. 24, 2022.

(30) Foreign Application Priority Data

Mar. 2, 2021 (JP) ................................ 2021-032354

(51) Int. Cl.

| | |
|---|---|
| ***G03F 7/038*** | (2006.01) |
| ***C07D 317/24*** | (2006.01) |
| ***C07D 317/72*** | (2006.01) |
| ***C07D 493/10*** | (2006.01) |
| ***C08F 212/14*** | (2006.01) |
| ***C08F 220/18*** | (2006.01) |
| ***C08F 220/28*** | (2006.01) |
| ***C08F 220/30*** | (2006.01) |
| ***G03F 7/039*** | (2006.01) |

(52) U.S. Cl.

CPC ........... *G03F 7/038* (2013.01); *C07D 317/24* (2013.01); *C07D 317/72* (2013.01); *C07D 493/10* (2013.01); *C08F 212/22* (2020.02); *C08F 220/1807* (2020.02); *C08F 220/283* (2020.02); *C08F 220/303* (2020.02); *G03F 7/039* (2013.01)

(58) Field of Classification Search

CPC .............. C08F 220/282; C08F 220/283; C08F 220/36

See application file for complete search history.

(56) References Cited

U.S. PATENT DOCUMENTS

2004/0248031 A1* 12/2004 Ansai .................. C07D 317/18 549/228
2012/0288794 A1* 11/2012 Bae ...................... C08F 220/20 526/270
2017/0031243 A1* 2/2017 Hatakeyama ......... G03F 7/0046
2017/0329223 A1* 11/2017 Masuyama ....... C08F 220/1811
2019/0079399 A1* 3/2019 Fukushima ........... C07C 43/247
2023/0087940 A1* 3/2023 Oka ...................... G03F 7/0392 430/270.1

FOREIGN PATENT DOCUMENTS

JP 5556765 B2 7/2014
KR 1020120061757 A 6/2012
KR 1020140051083 A 4/2014
KR 20180076823 A * 7/2018 .............. C08L 33/08

OTHER PUBLICATIONS

Machine translation of KR 2018-0076823 (no date) (Year: 0000).*
Machine translation of KR 2014-0051083 (no date) (Year: 0000).*
Office Action issued Jun. 11, 2025, in corresponding Japanese Patent Application No. 2023-503764 (with machine English translation), 4 pages.
Office Action issued Jul. 10, 2025, in corresponding Korean Patent Application No. 10-2023-7027220 (with English translation), 12 pages.
English translation of the International Preliminary Report on Patentability and Written Opinion issued Sep. 14, 2023 in PCT/JP2022/007670, 5 pages.
International Search Report issued May 17, 2022 in PCT/JP2022/007670, 2 pages.

* cited by examiner

*Primary Examiner* — Amanda C. Walke
(74) *Attorney, Agent, or Firm* — Element IP, PLC

(57) ABSTRACT

A radiation-sensitive resin composition includes a resin including a structural unit represented by formula (1), a radiation-sensitive acid generator, and a solvent. $R^1$ is a hydrogen atom, a fluorine atom, or the like. $R^2$ and $R^3$ each independently represent a monovalent hydrocarbon group having 1 to 10 carbon atoms, or the like. $R^4$ is a hydrogen atom, a monovalent hydrocarbon group having 1 to 10 carbon atoms, or the like. $R^5$ and $R^6$ each independently represent a hydrogen atom, a monovalent hydrocarbon group having 1 to 10 carbon atoms, or the like. $R^7$ and $R^8$ each independently represent a hydrogen atom, a monovalent hydrocarbon group having 1 to 10 carbon atoms, or the like. $R^9$ and $R^{10}$ each independently represent a monovalent organic group having 1 to 10 carbon atoms, or the like.

(1)

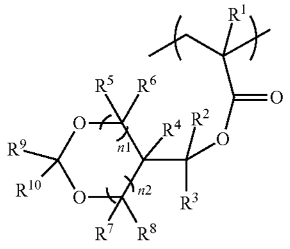

20 Claims, No Drawings

RADIATION-SENSITIVE RESIN COMPOSITION, METHOD FOR FORMING RESIST PATTERN, POLYMER, AND COMPOUND

REFERENCE TO RELATED APPLICATIONS

This application is a continuation-in-part application of PCT/JP2022/007670, which claims priority from Japanese Patent Application No. 2021-032354 filed on Mar. 2, 2021. The entire disclosure of these application is incorporated herein by reference.

BACKGROUND ART

The present invention relates to a radiation-sensitive resin composition, a method for forming a resist pattern, a polymer and a compound.

A photolithography technology using a resist composition has been used for the formation of a fine circuit in a semiconductor device. As a representative procedure, for example, a resist pattern is formed on a substrate by generating an acid by irradiating a coating film of the resist composition with radiation through a mask pattern, and then reacting in the presence of the acid as a catalyst to generate a difference in the solubility of a resin into an alkaline or organic developer between an exposed area and an unexposed area.

In the photolithography technology, the micronization of the pattern is promoted by using short-wavelength radiation such as an ArF excimer laser or by using an immersion exposure method (liquid immersion lithography) in which exposure is performed in a state in which a space between a lens of an exposure apparatus and a resist film is filled with a liquid medium.

While efforts for further technological development are in progress, a technique has been proposed in which a quencher (diffusion controlling agent) is blended in a resist composition, and an acid diffused to an unexposed area is captured by a salt exchange reaction to improve lithographic performance with ArF exposure (see, JP-B-5556765). In addition, as a next-generation technology, lithography using shorter-wavelength radiation such as an electron beam, an X-ray, and extreme ultraviolet ray (EUV) has also been explored.

SUMMARY OF THE INVENTION

According to an aspect of the present invention, a radiation-sensitive resin composition includes: a resin including a structural unit represented by formula (1); a radiation-sensitive acid generator; and a solvent.

(1)

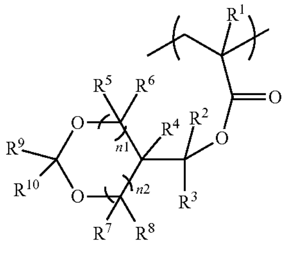

In the formula (1), $R^1$ is a hydrogen atom, a fluorine atom, a methyl group, or a trifluoromethyl group; $R^2$ and $R^3$ each independently represent a monovalent hydrocarbon group having 1 to 10 carbon atoms, or taken together represent a divalent cyclic hydrocarbon group having 3 to 20 carbon atoms together with the carbon atom to which $R^2$ and $R^3$ are bonded; $R^4$ is a hydrogen atom or a monovalent hydrocarbon group having 1 to 10 carbon atoms; $R^5$ and $R^6$ each independently represent a hydrogen atom or a monovalent hydrocarbon group having 1 to 10 carbon atoms, or taken together represent a divalent cyclic hydrocarbon group having 3 to 20 carbon atoms together with the carbon atoms to which $R^5$ and $R^6$ are bonded; $R^7$ and $R^8$ each independently represent a hydrogen atom or a monovalent hydrocarbon group having 1 to 10 carbon atoms, or taken together represent a divalent cyclic hydrocarbon group having 3 to 20 carbon atoms together with the carbon atoms to which $R^7$ and $R^8$ are bonded; $R^9$ and $R^{10}$ each independently represent a monovalent organic group having 1 to 10 carbon atoms, or taken together represent a 3- to 30-membered divalent cyclic organic group together with the carbon atom to which $R^9$ and $R^{10}$ are bonded; n1 is an integer of 1 to 4, and when n1 is 2 or more, a plurality of $R^5$ are the same or different from each other, and a plurality of $R^6$ are the same or different from each other; and n2 is an integer of 0 to 3, and when n2 is 2 or more, a plurality of $R^7$ are the same or different from each other, a plurality of $R^8$ are the same or different from each other.

According to another aspect of the present invention, a method for forming a resist pattern, includes: directly or indirectly applying the above-described radiation-sensitive resin composition to a substrate to form a resist film; exposing the resist film to light; and developing the exposed resist film.

According to a further aspect of the present invention, a polymer includes a structural unit represented by formula (1).

(1)

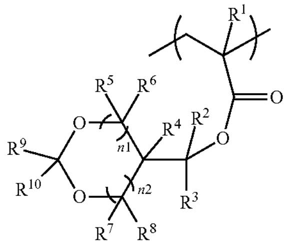

According to a further aspect of the present invention, a compound is represented by formula (3).

(3)

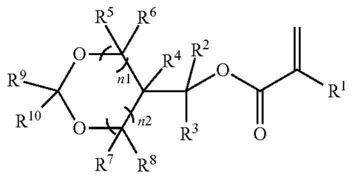

$R^1$ to $R^{10}$ are each as defined in formula (1).

DETAILED DESCRIPTION

As used herein, the words "a" and "an" and the like carry the meaning of "one or more." When an amount, concentration, or other value or parameter is given as a range, and/or its description includes a list of upper and lower values, this is to be understood as specifically disclosing all integers and fractions within the given range, and all ranges formed from any pair of any upper and lower values, regardless of whether subranges are separately disclosed. Where a range of numerical values is recited herein, unless otherwise stated, the range is intended to include the endpoints thereof, as well as all integers and fractions within the range. As an example, a stated range of 1-10 fully describes and includes the independent subrange 3.4-7.2 as does the following list of values: 1, 4, 6, 10.

That is, the present disclosure relates, in one embodiment, to a radiation-sensitive resin composition including:

a resin having a structural unit represented by formula (1) below (hereinafter also referred to as "structural unit (α)");

a radiation-sensitive acid generator; and a solvent,

[Formula 1]

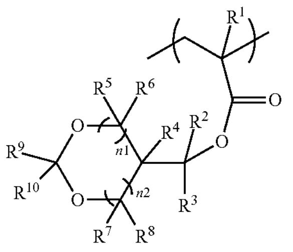

(1)

(in formula (1), $R^1$ is a hydrogen atom, a fluorine atom, a methyl group, or a trifluoromethyl group;

$R^2$ and $R^3$ each independently represent a monovalent hydrocarbon group having 1 to 10 carbon atoms or a divalent cyclic hydrocarbon group having 3 to 20 carbon atoms in which such groups are combined with each other and which is constituted of such groups together with the carbon atoms to which such groups are bonded;

$R^4$ is a hydrogen atom or a monovalent hydrocarbon group having 1 to 10 carbon atoms;

$R^5$ and $R^6$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded;

$R^7$ and $R^8$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded;

$R^9$ and $R^{10}$ each independently represent a monovalent organic group having 1 to 10 carbon atoms or a 3- to 30-membered divalent cyclic organic group in which such groups are combined with each other and which is constituted of such groups together with the carbon atoms to which such groups are bonded;

n1 is an integer of 1 to 4, and when n1 is 2 or more, a plurality of $R^5$ and $R^6$ are the same or different from each other; and n2 is an integer of 0 to 3, and when n2 is 2 or more, a plurality of $R^7$ and $R^8$ are the same or different from each other).

Since the radiation-sensitive resin composition of the present disclosure contains the resin having the structural unit (α), the composition can exhibit superior sensitivity, LWR performance, pattern rectangularity, and the like at the time of resist pattern formation. Since both an acrylate structural moiety and an acetal structural moiety of the structural unit (α) can be dissociated by an acid by exposure, it is presumed that the structural unit (α) affects the improvement of the pattern rectangularity in particular, together with the excellent sensitivity and LWR performance. The scope of the right of the present invention is not necessarily limited by this presumption of the mechanism of action.

In the present disclosure, examples of the organic group include a monovalent hydrocarbon group, a group containing a divalent hetero atom-containing group between two adjacent carbon atoms of the monovalent hydrocarbon group, and groups resulting from the hydrocarbon group and the group containing a divalent hetero atom-containing group by substituting some or all of the hydrogen atoms contained therein with a monovalent hetero atom-containing group.

In the present disclosure, the "hydrocarbon group" includes a chain hydrocarbon group, an alicyclic hydrocarbon group, and an aromatic hydrocarbon group unless any particular limitation is imposed on this element. The "hydrocarbon group" includes a saturated hydrocarbon group and an unsaturated hydrocarbon group. The "chain hydrocarbon group" refers to a hydrocarbon group that does not include any cyclic structure and is composed only of a chain structure, and includes both a linear hydrocarbon group and a branched hydrocarbon group. The "alicyclic hydrocarbon group" refers to a hydrocarbon group that includes only an alicyclic structure as a ring structure and does not include any aromatic ring structure and includes both a monocyclic alicyclic hydrocarbon group and a polycyclic alicyclic hydrocarbon group. However, it is not necessary for the alicyclic hydrocarbon group to be composed only of an alicyclic structure, and the alicyclic hydrocarbon group may include a chain structure in a part thereof. The "aromatic hydrocarbon group" refers to a hydrocarbon group that includes an aromatic ring structure as a ring structure. However, it is not necessary for the aromatic hydrocarbon group to be composed only of an aromatic ring structure, and the aromatic hydrocarbon group may include a chain structure or an alicyclic structure in a part thereof.

The present disclosure relates, in another embodiment, to a method for forming a resist pattern, the method including the steps of:

directly or indirectly applying the radiation-sensitive resin composition to a substrate to form a resist film;

exposing the resist film to light; and developing the exposed resist film.

Since the method for forming a resist pattern of the present disclosure includes the step using the above-described radiation-sensitive resin composition, the method can be utilized, for example, for good pattern formation superior in sensitivity, LWR performance, pattern rectangularity, and the like.

On the other hand, the present disclosure relates, in another embodiment, to a polymer (hereinafter also referred to as "polymer (1)") having a structural unit represented by formula (1) below (hereinafter also referred to as "structural unit (α)"):

[Formula 2]

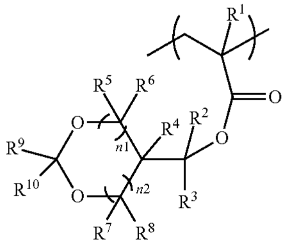

(1)

(in formula (1), $R^1$ is a hydrogen atom, a fluorine atom, a methyl group, or a trifluoromethyl group;

$R^2$ and $R^3$ each independently represent a monovalent hydrocarbon group having 1 to 10 carbon atoms or a divalent cyclic hydrocarbon group having 3 to 20 carbon atoms in which such groups are combined with each other and which is constituted of such groups together with the carbon atoms to which such groups are bonded;

$R^4$ is a hydrogen atom or a monovalent hydrocarbon group having 1 to 10 carbon atoms;

$R^5$ and $R^6$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded;

$R^7$ and $R^8$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded;

$R^9$ and $R^{10}$ each independently represent a monovalent organic group having 1 to 10 carbon atoms or a 3- to 30-membered divalent cyclic organic group in which such groups are combined with each other and which is constituted of such groups together with the carbon atoms to which such groups are bonded;

n1 is an integer of 1 to 4, and when n1 is 2 or more, a plurality of $R^5$ and $R^6$ are the same or different from each other; and n2 is an integer of 0 to 3, and when n2 is 2 or more, a plurality of $R^7$ and $R^8$ are the same or different from each other).

Since the polymer (1) of the present disclosure has the structural unit (α), the above-described radiation-sensitive resin composition can be produced using this polymer.

In addition, the present disclosure relates, in another embodiment, to a compound represented by formula (3) below (hereinafter also referred to as "compound (1)"):

[Formula 3]

[Formula 3]

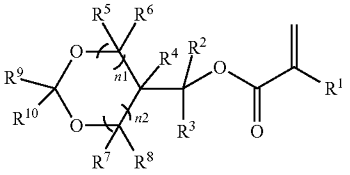

(3)

(in formula (1), $R^1$ is a hydrogen atom, a fluorine atom, a methyl group, or a trifluoromethyl group;

$R^2$ and $R^3$ each independently represent a monovalent hydrocarbon group having 1 to 10 carbon atoms or a divalent cyclic hydrocarbon group having 3 to 20 carbon atoms in which such groups are combined with each other and which is constituted of such groups together with the carbon atoms to which such groups are bonded;

$R^4$ is a hydrogen atom or a monovalent hydrocarbon group having 1 to 10 carbon atoms;

$R^5$ and $R^6$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded;

$R^7$ and $R^8$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded;

$R^9$ and $R^{10}$ each independently represent a monovalent organic group having 1 to 10 carbon atoms or a 3- to 30-membered divalent cyclic organic group in which such groups are combined with each other and which is constituted of such groups together with the carbon atoms to which such groups are bonded;

n1 is an integer of 1 to 4, and when n1 is 2 or more, a plurality of $R^5$ and $R^6$ are the same or different from each other; and n2 is an integer of 0 to 3, and when n2 is 2 or more, a plurality of $R^7$ and $R^8$ are the same or different from each other).

Since the compound (1) of the present disclosure has the above-described chemical structure, the above-described polymer can be produced using the compound (1) as a monomer component.

Hereinbelow, embodiments of the present invention will specifically be described, but the present invention is not limited to these embodiments.

<Radiation-Sensitive Resin Composition>

A radiation-sensitive resin composition (hereinafter also simply referred to as "composition") according to the present embodiment includes a resin having a structural unit (α), a radiation-sensitive acid generator, and a solvent. The composition may further contain other optional components as long as the effects of the present invention are not impaired. When the radiation-sensitive resin composition contains the resin having the structural unit (α), high levels of sensitivity, LWR performance, and pattern rectangularity can be imparted to the radiation-sensitive resin composition.

(Resin Having Structural Unit (α))

The resin having the structural unit (α) is an assembly of polymers having a structural unit containing an acid-dissociable group (this structural unit is hereinafter also referred to as "structural unit (I)") (this resin is hereinafter also referred to as "base resin"). The structural unit (α) is also an acid-dissociable group. While the resin contains the structural unit (α) as an acid-dissociable group (structural unit (I)), the resin may further contain another acid-dissociable group. The "acid-dissociable group" refers to a group that substitutes for a hydrogen atom of a carboxy group, a phenolic hydroxy group, an alcoholic hydroxy group, a sulfo group, or the like and is dissociated by the action of an acid. The radiation-sensitive resin composition of the present disclosure is superior in patternability because the resin has the structural unit (I).

In addition to the structural unit (I), the base resin preferably has a structural unit (II) containing at least one selected from the group consisting of a lactone structure, a cyclic carbonate structure, and a sultone structure, which are described later, and may have other structural units than the structural units (I) and (II). Hereinbelow, each of the structural units will be described.

[Structural Unit (I)]

The structural unit (I) is a structural unit containing an acid-dissociable group, and the resin contains the structural unit (α).

[Structural Unit (α)]

The structural unit (α) is represented by the above formula (1).

In the above formula (1), $R^1$ is a hydrogen atom, a fluorine atom, a methyl group, or a trifluoromethyl group.

In the above formula (1), $R^2$ and $R^3$ each independently represent a monovalent hydrocarbon group having 1 to 10 carbon atoms or a divalent cyclic hydrocarbon group having 3 to 20 carbon atoms in which such groups are combined with each other and which is constituted of such groups together with the carbon atoms to which such groups are bonded.

Examples of the monovalent hydrocarbon group having 1 to 10 carbon atoms represented by $R^2$ and $R^3$ in the above formula (1) include chain hydrocarbon groups having 1 to 10 carbon atoms, monovalent alicyclic hydrocarbon groups having 3 to 10 carbon atoms, and monovalent aromatic hydrocarbon groups having 6 to 10 carbon atoms.

Examples of the chain hydrocarbon groups having 1 to 10 carbon atoms represented by $R^2$ and $R^3$ in the above formula (1) include linear or branched chain saturated hydrocarbon groups having 1 to 10 carbon atoms and linear or branched chain unsaturated hydrocarbon groups having 1 to 10 carbon atoms.

Examples of the monovalent alicyclic hydrocarbon group having 3 to 10 carbon atoms represented by $R^2$ and $R^3$ in the above formula (1) include monocyclic or polycyclic saturated hydrocarbon groups and monocyclic or polycyclic unsaturated hydrocarbon groups. Examples of the monocyclic saturated hydrocarbon group include a cyclopentyl group, a cyclohexyl group, a cycloheptyl group, and a cyclooctyl group. Examples of the polycyclic cycloalkyl group include bridged alicyclic hydrocarbon groups such as a norbornyl group and an adamantyl group. Examples of the monocyclic unsaturated hydrocarbon group include monocyclic cycloalkenyl groups such as a cyclopropenyl group, a cyclobutenyl group, a cyclopentenyl group, and a cyclohexenyl group. Examples of the polycyclic unsaturated hydrocarbon group include polycyclic cycloalkenyl groups such as a norbornenyl group. It is to be noted that the bridged alicyclic hydrocarbon group refers to a polycyclic alicyclic hydrocarbon group in which two carbon atoms that constitute an alicyclic ring and not adjacent to each other are bonded by a bonding chain containing one or more carbon atoms.

Examples of the monovalent aromatic hydrocarbon group having 6 to 10 carbon atoms represented by $R^2$ and $R^3$ in the above formula (1) include aryl groups, such as a phenyl group, a tolyl group, a xylyl group, a naphthyl group, and an anthryl group; and aralkyl groups, such as a benzyl group, a phenethyl group, and a naphthylmethyl group.

The divalent cyclic hydrocarbon group having 3 to 20 carbon atoms represented by $R^2$ and $R^3$ in the above formula (1) in which such groups are combined with each other and which is constituted of such groups together with the carbon atoms to which such groups are bonded is not particularly limited as long as it is a group formed by removing two hydrogen atoms from the same carbon atom constituting the carbon ring of the alicyclic hydrocarbon having the above number of carbon atoms.

In the above formula (1), $R^4$ is a hydrogen atom or a monovalent hydrocarbon group having 1 to 10 carbon atoms.

Examples of the monovalent hydrocarbon group having 1 to 10 carbon atoms represented by $R^4$ in the above formula (1) include chain hydrocarbon groups having 1 to 10 carbon atoms, monovalent alicyclic hydrocarbon groups having 3 to 10 carbon atoms, and monovalent aromatic hydrocarbon groups having 6 to 10 carbon atoms.

Examples of the chain hydrocarbon group having 1 to 10 carbon atoms represented by $R^4$ in the above formula (1) include linear or branched chain saturated hydrocarbon groups having 1 to 10 carbon atoms and linear or branched chain unsaturated hydrocarbon groups having 1 to 10 carbon atoms.

Examples of the monovalent alicyclic hydrocarbon group having 3 to 10 carbon atoms represented by $R^4$ in the above formula (1) include monocyclic or polycyclic saturated hydrocarbon groups and monocyclic or polycyclic unsaturated hydrocarbon groups. Examples of the monocyclic saturated hydrocarbon group include a cyclopentyl group, a cyclohexyl group, a cycloheptyl group, and a cyclooctyl group. Examples of the polycyclic cycloalkyl group include bridged alicyclic hydrocarbon groups such as a norbornyl group and an adamantyl group. Examples of the monocyclic unsaturated hydrocarbon group include monocyclic cycloalkenyl groups such as a cyclopropenyl group, a cyclobutenyl group, a cyclopentenyl group, and a cyclohexenyl group. Examples of the polycyclic unsaturated hydrocarbon group include polycyclic cycloalkenyl groups such as a norbornenyl group. It is to be noted that the bridged alicyclic hydrocarbon group refers to a polycyclic alicyclic hydrocarbon group in which two carbon atoms that constitute an alicyclic ring and not adjacent to each other are bonded by a bonding chain containing one or more carbon atoms.

Examples of the monovalent aromatic hydrocarbon group having 6 to 10 carbon atoms represented by $R^4$ in the above formula (1) include aryl groups, such as a phenyl group, a tolyl group, a xylyl group, a naphthyl group, and an anthryl group; and aralkyl groups, such as a benzyl group, a phenethyl group, and a naphthylmethyl group.

In the above formula (1), $R^5$ and $R^6$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded.

Examples of the monovalent hydrocarbon group having 1 to 10 carbon atoms represented by $R^5$ and $R^6$ in the above formula (1) include chain hydrocarbon groups having 1 to 10 carbon atoms, monovalent alicyclic hydrocarbon groups having 3 to 10 carbon atoms, and monovalent aromatic hydrocarbon groups having 6 to 10 carbon atoms.

Examples of the chain hydrocarbon groups having 1 to 10 carbon atoms represented by $R^5$ and $R^6$ in the above formula (1) include linear or branched chain saturated hydrocarbon groups having 1 to 10 carbon atoms and linear or branched chain unsaturated hydrocarbon groups having 1 to 10 carbon atoms.

Examples of the monovalent alicyclic hydrocarbon group having 3 to 10 carbon atoms represented by $R^5$ and $R^6$ in the above formula (1) include monocyclic or polycyclic saturated hydrocarbon groups and monocyclic or polycyclic unsaturated hydrocarbon groups. Examples of the monocyclic saturated hydrocarbon group include a cyclopentyl group, a cyclohexyl group, a cycloheptyl group, and a cyclooctyl group. Examples of the polycyclic cycloalkyl group include bridged alicyclic hydrocarbon groups such as a norbornyl group and an adamantyl group. Examples of the monocyclic unsaturated hydrocarbon group include monocyclic cycloalkenyl groups such as a cyclopropenyl group, a cyclobutenyl group, a cyclopentenyl group, and a cyclohexenyl group. Examples of the polycyclic unsaturated hydrocarbon group include polycyclic cycloalkenyl groups such as a norbornenyl group. It is to be noted that the bridged alicyclic hydrocarbon group refers to a polycyclic alicyclic hydrocarbon group in which two carbon atoms that constitute an alicyclic ring and not adjacent to each other are bonded by a bonding chain containing one or more carbon atoms.

Examples of the monovalent aromatic hydrocarbon group having 6 to 10 carbon atoms represented by $R^5$ and $R^6$ in the above formula (1) include aryl groups, such as a phenyl group, a tolyl group, a xylyl group, a naphthyl group, and an anthryl group; and aralkyl groups, such as a benzyl group, a phenethyl group, and a naphthylmethyl group.

The divalent cyclic hydrocarbon group having 3 to 20 carbon atoms represented by $R^5$ and $R^6$ in the above formula (1) in which such groups are combined with each other and which is constituted of such groups together with the carbon atoms to which such groups are bonded is not particularly limited as long as it is a group formed by removing two hydrogen atoms from the same carbon atom constituting the carbon ring of the alicyclic hydrocarbon having the above number of carbon atoms.

In the above formula (1), $R^7$ and $R^8$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded.

Examples of the monovalent hydrocarbon group having 1 to 10 carbon atoms represented by $R^7$ and $R^8$ in the above formula (1) include chain hydrocarbon groups having 1 to 10 carbon atoms, monovalent alicyclic hydrocarbon groups having 3 to 10 carbon atoms, and monovalent aromatic hydrocarbon groups having 6 to 10 carbon atoms.

Examples of the chain hydrocarbon groups having 1 to 10 carbon atoms represented by $R^7$ and $R^8$ in the above formula (1) include linear or branched saturated hydrocarbon groups having 1 to 10 carbon atoms and linear or branched chain unsaturated hydrocarbon groups having 1 to 10 carbon atoms.

Examples of the monovalent alicyclic hydrocarbon group having 3 to 10 carbon atoms represented by $R^7$ and $R^8$ in the above formula (1) include monocyclic or polycyclic saturated hydrocarbon groups and monocyclic or polycyclic unsaturated hydrocarbon groups. Examples of the monocyclic saturated hydrocarbon group include a cyclopentyl group, a cyclohexyl group, a cycloheptyl group, and a cyclooctyl group. Examples of the polycyclic cycloalkyl group include bridged alicyclic hydrocarbon groups such as a norbornyl group and an adamantyl group. Examples of the monocyclic unsaturated hydrocarbon group include monocyclic cycloalkenyl groups such as a cyclopropenyl group, a cyclobutenyl group, a cyclopentenyl group, and a cyclohexenyl group. Examples of the polycyclic unsaturated hydrocarbon group include polycyclic cycloalkenyl groups such as a norbornenyl group. It is to be noted that the bridged alicyclic hydrocarbon group refers to a polycyclic alicyclic hydrocarbon group in which two carbon atoms that constitute an alicyclic ring and not adjacent to each other are bonded by a bonding chain containing one or more carbon atoms.

Examples of the monovalent aromatic hydrocarbon group having 6 to 10 carbon atoms represented by $R^7$ and $R^8$ in the above formula (1) include aryl groups, such as a phenyl group, a tolyl group, a xylyl group, a naphthyl group, and an anthryl group; and aralkyl groups, such as a benzyl group, a phenethyl group, and a naphthylmethyl group.

The divalent cyclic hydrocarbon group having 3 to 20 carbon atoms represented by $R^7$ and $R^8$ in the above formula (1) in which such groups are combined with each other and which is constituted of such groups together with the carbon atoms to which such groups are bonded is not particularly limited as long as it is a group formed by removing two hydrogen atoms from the same carbon atom constituting the carbon ring of the alicyclic hydrocarbon having the above number of carbon atoms.

In the above formula (1), $R^9$ and $R^{10}$ each independently represent a monovalent organic group having 1 to 10 carbon atoms or a 3- to 30-membered divalent cyclic organic group in which such groups are combined with each other and which is constituted of such groups together with the carbon atoms to which such groups are bonded.

Examples of the monovalent organic group having 1 to 10 carbon atoms represented by $R^9$ and $R^{10}$ in the above formula (1) include a monovalent hydrocarbon group having 1 to 10 carbon atoms, a group containing a divalent hetero atom-containing group between two adjacent carbon atoms of the monovalent hydrocarbon group, and groups resulting from the hydrocarbon group and the group containing a divalent hetero atom-containing group by substituting some or all of the hydrogen atoms contained therein with a monovalent hetero atom-containing group.

Examples of the monovalent hydrocarbon group having 1 to 10 carbon atoms represented by $R^9$ and $R^{10}$ in the above formula (1) include chain hydrocarbon groups having 1 to 10 carbon atoms, monovalent alicyclic hydrocarbon groups having 3 to 10 carbon atoms, and monovalent aromatic hydrocarbon groups having 6 to 10 carbon atoms.

Examples of the chain hydrocarbon groups having 1 to 10 carbon atoms represented by $R^9$ and $R^{10}$ in the above formula (1) include linear or branched chain saturated hydrocarbon groups having 1 to 10 carbon atoms and linear or branched chain unsaturated hydrocarbon groups having 1 to 10 carbon atoms.

Examples of the monovalent alicyclic hydrocarbon group having 3 to 10 carbon atoms represented by $R^9$ and $R^{10}$ in the above formula (1) include monocyclic or polycyclic saturated hydrocarbon groups and monocyclic or polycyclic unsaturated hydrocarbon groups. Examples of the monocyclic saturated hydrocarbon group include a cyclopentyl group, a cyclohexyl group, a cycloheptyl group, and a cyclooctyl group. Examples of the polycyclic cycloalkyl group include bridged alicyclic hydrocarbon groups such as a norbornyl group and an adamantyl group. Examples of the monocyclic unsaturated hydrocarbon group include monocyclic cycloalkenyl groups such as a cyclopropenyl group, a cyclobutenyl group, a cyclopentenyl group, and a cyclohexenyl group. Examples of the polycyclic unsaturated hydrocarbon group include polycyclic cycloalkenyl groups such as a norbornenyl group. It is to be noted that the bridged alicyclic hydrocarbon group refers to a polycyclic alicyclic hydrocarbon group in which two carbon atoms that constitute an alicyclic ring and not adjacent to each other are bonded by a bonding chain containing one or more carbon atoms.

Examples of the monovalent aromatic hydrocarbon group having 6 to 10 carbon atoms represented by $R^9$ and $R^{10}$ in the above formula (1) include aryl groups, such as a phenyl group, a tolyl group, a xylyl group, a naphthyl group, and an anthryl group; and aralkyl groups, such as a benzyl group, a phenethyl group, and a naphthylmethyl group.

In the formula (1), the group containing a divalent hetero atom-containing group between two adjacent carbon atoms of the hydrocarbon group represented by $R^9$ and $R^{10}$ is not particularly limited as long as it is a group containing a divalent hetero atom-containing group such as an oxygen atom or a sulfur atom between two adjacent carbon atoms of the hydrocarbon group.

In the above formula (1), the group is not particularly limited as long as it is a group in which some or all of the hydrogen atoms contained in the group containing the divalent hetero atom-containing group represented by $R^9$ and $R^{10}$ are substituted with a monovalent hetero atom-containing group such as a fluorine atom or a chlorine atom.

The divalent cyclic organic group having 3 to 30 carbon atoms represented by $R^9$ and $R^{10}$ in the above formula (1) in which such groups are combined with each other and which is constituted of such groups together with the carbon atoms to which such groups are bonded is not particularly limited as long as it is a group formed by removing two hydrogen atoms from the same carbon atom constituting a cyclic structure having the above number of carbon atoms. Examples of the cyclic structure include an alicyclic structure having 3 to 30 carbon atoms, a lactone structure, a cyclic carbonate structure, and a sultone structure. These cyclic structures may be substituted with a halogen atom, a hydroxyl group, a monovalent organic group, or the like.

In the above formula (1), examples of the divalent cyclic organic group having 3 to 20 carbon atoms represented by $R^9$ and $R^{10}$ include groups represented by the following formulas (* represents a bonding site with each oxygen atom of an acetal ring structure).

[Formula 4]

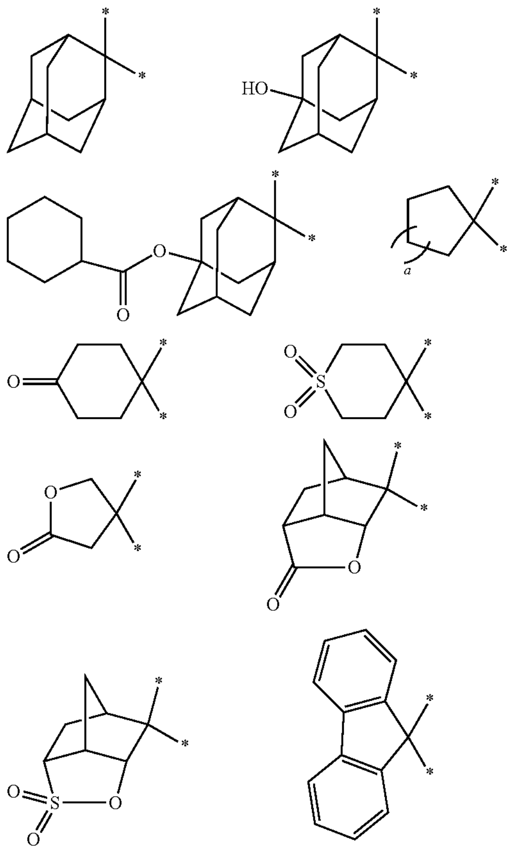

(In the formulas, a is an integer of 1 to 6.)

In the above formula (1), n1 is an integer of 1 to 4. When n1 is 2 or more, a plurality of $R^5$ and $R^6$ are the same or different from each other.

In the above formula (1), n2 is an integer of 0 to 3. When n2 is 2 or more, a plurality of $R^7$ and $R^8$ are the same or different from each other.

Examples of the monomer component for obtaining the structural unit (α) represented by the above formula (1) include compounds represented by the following formulas (M-1) to (M-25).

[Formula 5]

(M-1)

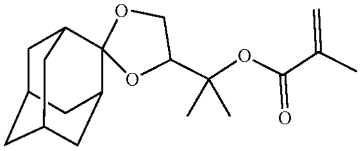

(M-2)

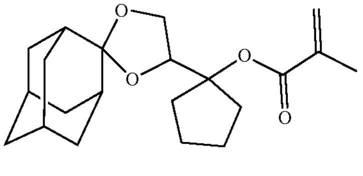

-continued
(M-3)
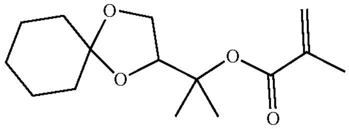
(M-4)
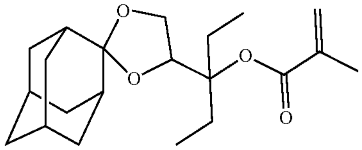
(M-5)
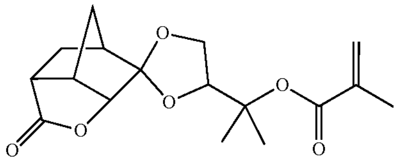
(M-6)
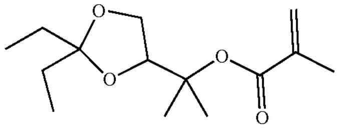
(M-7)
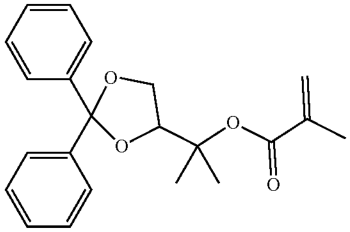
(M-8)
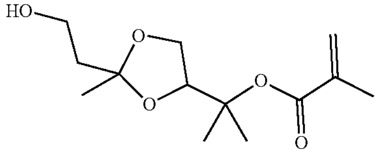
(M-9)
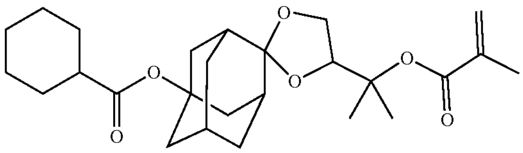
(M-10)
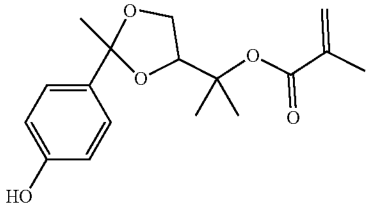
-continued
[Formula 6]
(M-11)
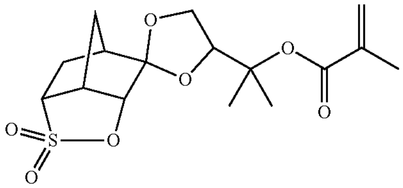
(M-12)
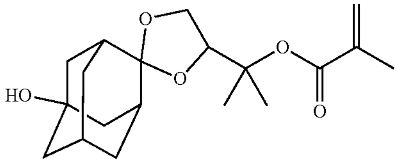
(M-13)
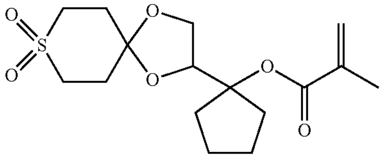
(M-14)
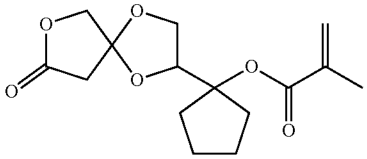
(M-15)
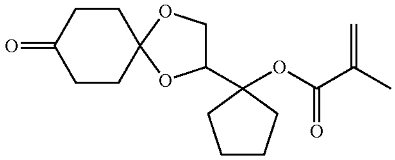
(M-16)
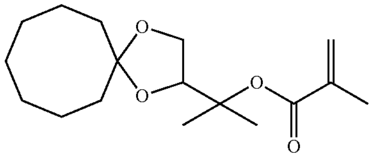
(M-17)
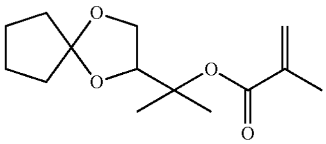
(M-18)
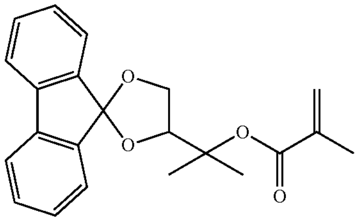

-continued (M-19)

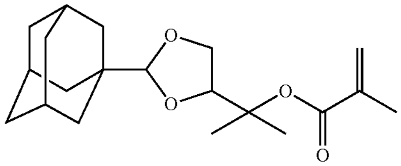

(M-20)

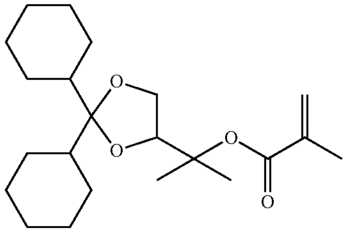

(M-21)

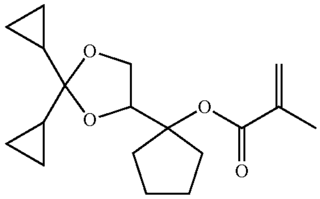

(M-22)

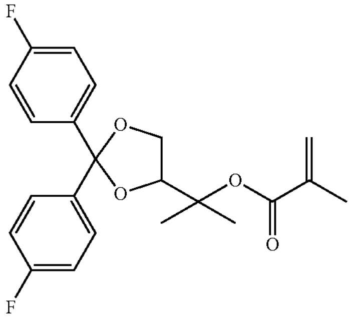

(M-23)

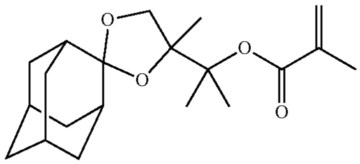

(M-24)

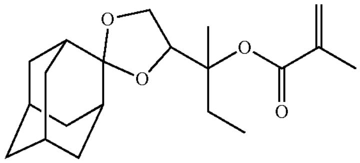

(M-25)

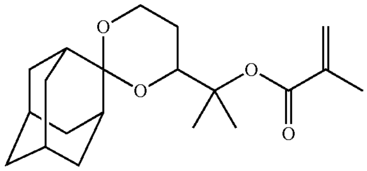

[Structural Unit (I) Other than Structural Unit (α)]

The structural unit (I) may contain other acid-dissociable groups than the structural unit (α). The structural unit (I) is not particularly limited as long as it contains an acid-dissociable group, and examples thereof include a structural unit having a tertiary alkyl ester moiety, a structural unit having a structure in which a hydrogen atom of a phenolic hydroxy group is substituted with a tertiary alkyl group, and a structural unit having an acetal bond. From the viewpoint of improving patternability, a structural unit represented by the following formula (2) (hereinafter also referred to as "structural unit (I-1)") is preferable.

[Formula 7]

(2)

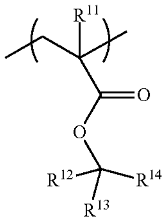

(In the formula (2), $R^{11}$ is a hydrogen atom, a fluorine atom, a methyl group, or a trifluoromethyl group.

$R^{12}$ is a monovalent hydrocarbon group having 1 to 20 carbon atoms.

$R^{13}$ and $R^{14}$ each independently are a monovalent chain hydrocarbon group having 1 to 10 carbon atoms or a monovalent alicyclic hydrocarbon group having 3 to 20 carbon atoms, or represent a divalent alicyclic hydrocarbon group having 3 to 20 carbon atoms in which such groups are combined with each other and which is constituted of such groups together with the carbon atoms to which such groups are bonded.)

In the above formula (2), from the viewpoint of the copolymerizability of a monomer that affords the structural unit (I), as $R^{11}$, a hydrogen atom and a methyl group are preferable, and a methyl group is more preferable.

Examples of the monovalent hydrocarbon group having 1 to 20 carbon atoms represented by $R^{12}$ in the above formula (2) include chain hydrocarbon groups having 1 to 20 carbon atoms, monovalent alicyclic hydrocarbon groups having 3 to 20 carbon atoms, and monovalent aromatic hydrocarbon groups having 6 to 20 carbon atoms.

Examples of the chain hydrocarbon group having 1 to 20 carbon atoms represented by $R^{12}$ in the above formula (2) include linear or branched chain saturated hydrocarbon groups having 1 to 20 carbon atoms and linear or branched chain unsaturated hydrocarbon groups having 1 to 20 carbon atoms.

Examples of the monovalent alicyclic hydrocarbon group having 3 to 20 carbon atoms represented by $R^{12}$ in the above formula (2) include monocyclic or polycyclic saturated hydrocarbon groups and monocyclic or polycyclic unsaturated hydrocarbon groups. Examples of the monocyclic saturated hydrocarbon group include a cyclopentyl group, a cyclohexyl group, a cycloheptyl group, a cyclooctyl group, a cycloundecanyl group, and a cyclododecanyl group. Examples of the polycyclic cycloalkyl group include bridged alicyclic hydrocarbon groups such as a norbornyl group and an adamantyl group. Examples of the monocyclic unsaturated hydrocarbon group include monocyclic cycloalkenyl groups such as a cyclopropenyl group, a cyclobutenyl group, a cyclopentenyl group, a cyclohexenyl group, and a cyclooctenyl group. Examples of the polycyclic unsaturated hydrocarbon group include polycyclic cycloalkenyl groups such as a norbornenyl group. It is to be noted that the bridged alicyclic hydrocarbon group refers to a polycyclic alicyclic hydrocarbon group in which two carbon atoms that constitute an alicyclic ring and not adjacent to each other are bonded by a bonding chain containing one or more carbon atoms.

Examples of the monovalent aromatic hydrocarbon group having 6 to 20 carbon atoms represented by $R^{12}$ in the above formula (2) include aryl groups, such as a phenyl group, a tolyl group, a xylyl group, a naphthyl group, an anthryl group, and a pyrenyl group; and aralkyl groups, such as a benzyl group, a phenethyl group, and a naphthylmethyl group.

Examples of the chain hydrocarbon groups having 1 to 10 carbon atoms represented by $R^{13}$ and $R^{14}$ in the above formula (2) include linear or branched chain saturated hydrocarbon groups having 1 to 10 carbon atoms and linear or branched chain unsaturated hydrocarbon groups having 1 to 10 carbon atoms.

Examples of the monovalent alicyclic hydrocarbon groups having 3 to 20 carbon atoms represented by $R^{13}$ and $R^{14}$ in the above formula (2) include monovalent monocyclic aliphatic hydrocarbon groups having 3 to 20 carbon atoms, and monovalent bridged alicyclic hydrocarbon groups having 6 to 20 carbon atoms.

Examples of the monovalent monocyclic aliphatic hydrocarbon groups having 3 to 20 carbon atoms represented by $R^{13}$ and $R^{14}$ in the above formula (2) include a cyclopropyl group, a cyclobutyl group, a cyclopentyl group, a cyclohexyl group, and a cyclooctyl group.

Examples of the monovalent bridged alicyclic hydrocarbon groups having 6 to 20 carbon atoms represented by $R^{13}$ and $R^{14}$ in the above formula (2) include a norbornyl group, an adamantyl group, a tricyclodecyl group, and a tetracyclododecyl group.

The divalent alicyclic hydrocarbon group having 3 to 20 carbon atoms represented by $R^{13}$ and $R^{14}$ in the above formula (2) and the carbon atoms to which these groups are bonded wherein these groups are combined with each other is not particularly limited as long as it is a group formed by removing two hydrogen atoms from the same carbon atom contained in the carbon ring of the alicyclic hydrocarbon having the aforementioned number of carbon atoms.

Examples of the structural unit (I) represented by the following formula (2) ("structural unit (I-1)") include structural units represented by the following formulas (2-1) to (2-7) (hereinafter, also referred to as "structural units (I-2-1) to (I-2-7)").

[Formula 8]

(2-1)

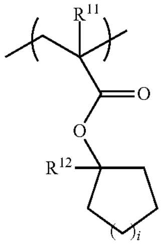

-continued (2-2)

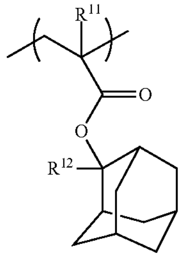

(2-3)

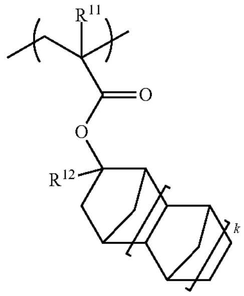

(2-4)

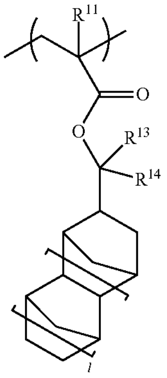

(2-5)

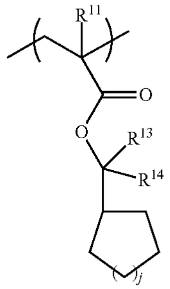

(2-6)

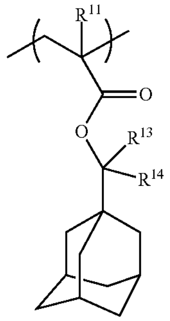

-continued (2-7)

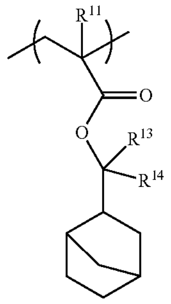

In the above formulas (2-1) to (2-7), $R^{11}$ to $R^{14}$ have the same definitions as those in the above formula (2).

In the above formula (2-1), i is an integer of 0 to 16. As i, 1 is preferable.

In the above formula (2-3), k is 0 to 1.

In the above formula (2-4), 1 is an integer of 0 to 2.

In the above formula (2-5), j is an integer of 0 to 16. As j, 1 is preferable.

In the above formulas (2-1) to (2-7), as $R^{12}$, a methyl group, an ethyl group, or an isopropyl group is preferable.

In the above formulas (2-1) to (2-7), as $R^{13}$ and $R^{14}$ each independently, a methyl group or an ethyl group is preferable.

The base resin may contain one type of the structural unit (I) or two or more types of the structural unit (I) in combination.

The content ratio of the structural unit (I) (a total content ratio when a plurality of types are contained) is preferably 10 mol % or more, more preferably 20 mol % or more, still more preferably 30 mol % or more, and particularly preferably 35 mol % or more based on all structural units constituting the base resin. The content ratio is preferably 80 mol % or less, more preferably 75 mol % or less, still more preferably 70 mol % or less, and particularly preferably 65 mol % or less. When the content ratio of the structural unit (I) is adjusted to within the above range, the patternability of the radiation-sensitive resin composition of the present disclosure can be further improved.

[Structural Unit (II)]

The structural unit (II) is a structural unit containing at least one structure selected from the group consisting of a lactone structure, a cyclic carbonate structure, and a sultone structure. When the base resin further has the structural unit (II), the solubility of the base resin in a developer can be adjusted, and as a result, the lithographic performance, such as resolution, of the resist film obtained from the radiation-sensitive resin composition of the present disclosure can be improved. In addition, the adhesion between a resist pattern formed from the base resin and a substrate can be improved.

Examples of the structural unit (II) include structural units represented by the following formulas (T-1) to (T-10).

[Formula 9]

(T-1)

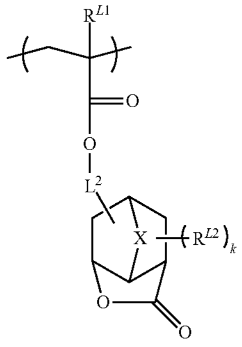

(T-2)

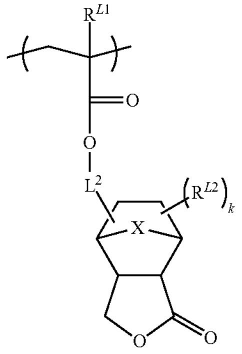

(T-3)

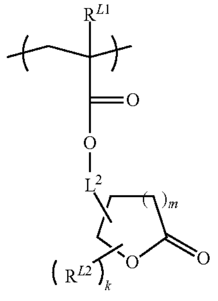

(T-4)

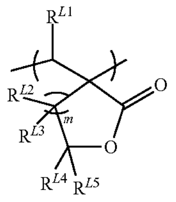

(T-5)

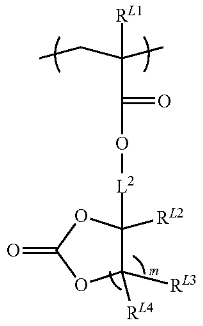

-continued (T-6)

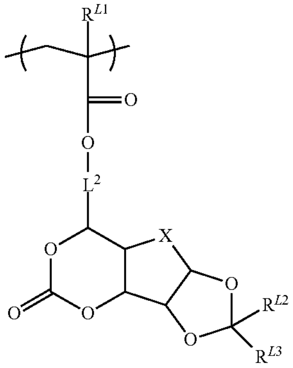

(T-7)

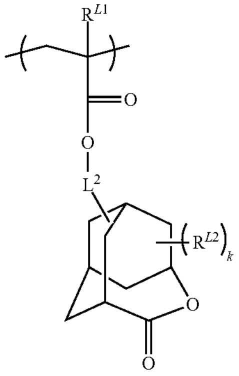

(T-8)

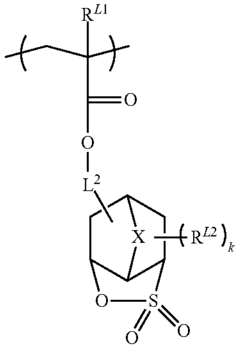

(T-9)

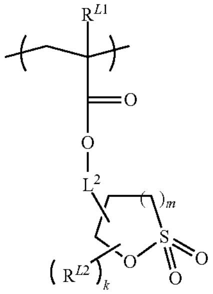

-continued (T-10)

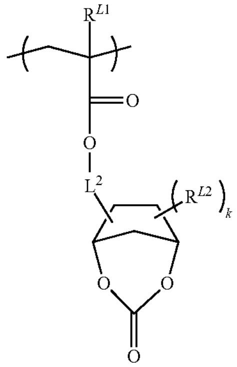

In the above formula, $R^{L1}$ is a hydrogen atom, a fluorine atom, a methyl group, or a trifluoromethyl group. $R^{L2}$ to $R^{L5}$ each independently are a hydrogen atom, an alkyl group having 1 to 4 carbon atoms, a cyano group, a trifluoromethyl group, a methoxy group, a methoxycarbonyl group, a hydroxy group, a hydroxymethyl group, or a dimethylamino group. $R^{L4}$ and $R^{L5}$ may be combined with each other and constitute a divalent alicyclic group having 3 to 8 carbon atoms together with the carbon atom to which they are bonded. $L^2$ is a single bond or a divalent linking group. X is an oxygen atom or a methylene group. k is integer of 0 to 3. m is an integer of 1 to 3.

Examples of the divalent alicyclic group having 3 to 8 carbon atoms in which $R^{L4}$ and $R^{L5}$ are combined with each other and which is constituted together with the carbon atoms to which they are bonded include a group having 3 to 8 carbon atoms, of a divalent alicyclic group having 3 to 20 carbon atoms in which the chain hydrocarbon groups represented by $R^{11}$ and $R^{12}$ in the above formula (5) or the alicyclic hydrocarbon groups are combined with each other and which is constituted together with the carbon atoms to which such groups are bonded. One or more hydrogen atoms on the alicyclic group may be replaced by a hydroxy group.

Examples of the divalent linking group represented by $L^2$ include a divalent linear or branched hydrocarbon group having 1 to 10 carbon atoms, a divalent alicyclic hydrocarbon group having 4 to 12 carbon atoms, and a group composed of one or more among these hydrocarbon groups and at least one group among —CO—, —O—, —NH—, and —S.

Among them, the structural unit (II) is preferably a structural unit containing a lactone structure, more preferably a structural unit containing a norbornane lactone structure, and still more preferably a structural unit derived from norbornane lactone-yl (meth)acrylate.

The content ratio of the structural unit (II) is preferably 20 mol % or more, more preferably 25 mol % or more, and still more preferably 30 mol % or more based on all structural units constituting the base resin. The content ratio by percent is preferably 80 mol % or less, more preferably 75 mol % or less, and still more preferably 70 mol % or less. When the content ratio of the structural unit (II) is adjusted to within the range, the lithographic performance, such as resolution, of a resist film obtained from the radiation-sensitive resin composition of the present disclosure and the adhesion between a resist patter formed and a substrate can be further improved.

[Structural Unit (III)]

The base resin optionally has other structural units in addition to the structural units (I) and (II). Examples of the other structural unit include a structural unit (III) containing a polar group (excluding those corresponding to the structural unit (II)). When the base resin further has the structural unit (III), the solubility of the base resin in a developer can be adjusted, and as a result, the lithographic performance, such as resolution, of the resist film obtained from the radiation-sensitive resin composition of the present disclosure can be improved. Examples of the polar group include a hydroxy group, a carboxy group, a cyano group, a nitro group, and a sulfonamide group. Among them, a hydroxy group and a carboxy group are preferable, and a hydroxy group is more preferable.

Examples of the structural unit (III) include structural units represented by the following formulas.

[Formula 10]

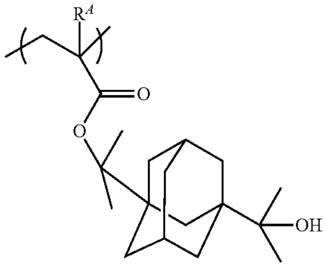

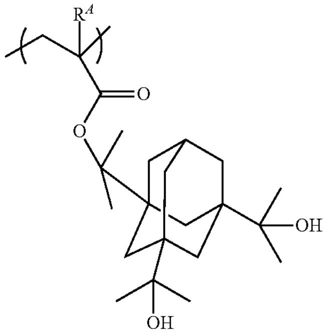

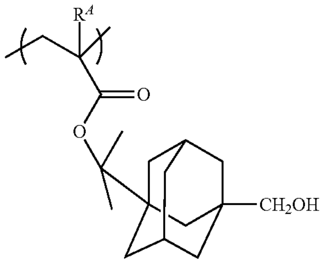

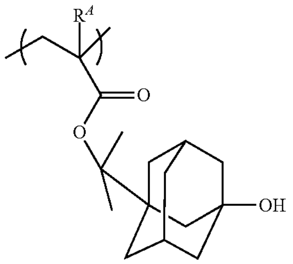

-continued

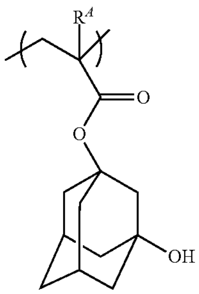

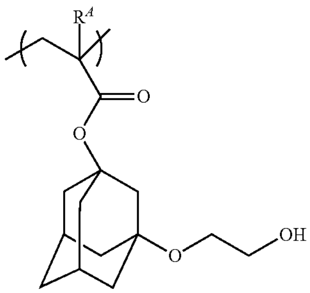

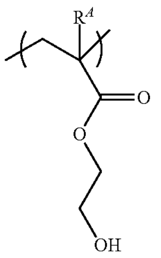

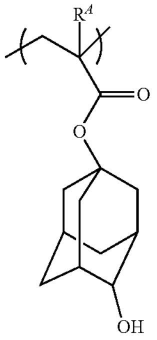

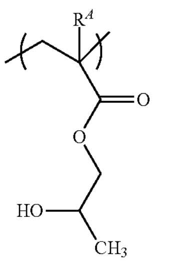

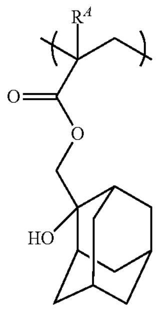

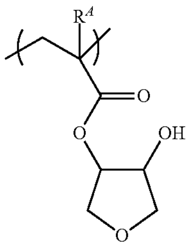

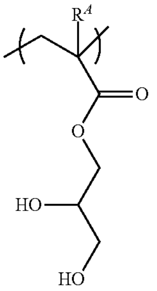

-continued

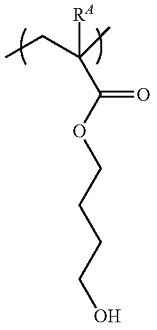

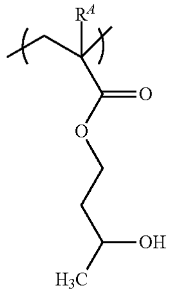

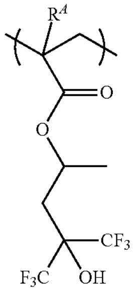

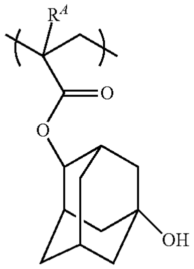

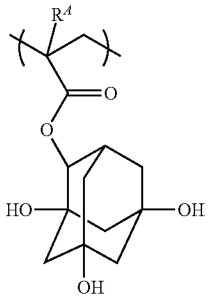

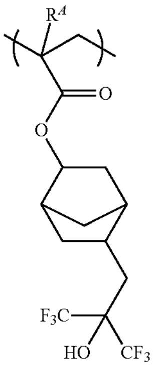

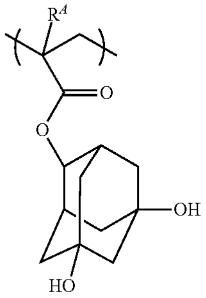

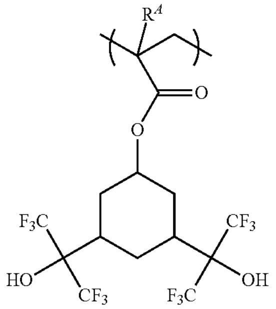

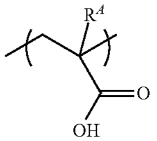

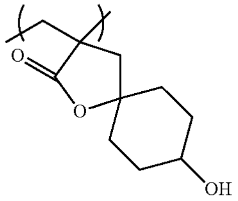

-continued

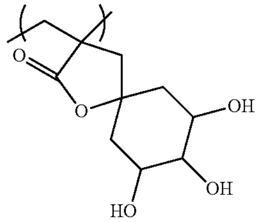

In the above formulas, $R^A$ is a hydrogen atom, a fluorine atom, a methyl group, or a trifluoromethyl group.

When the base resin has the structural unit (III) having a polar group, the content ratio of the structural unit (III) is preferably 5 mol % or more, more preferably 8 mol % or more, and still more preferably 10 mol % or more based on all structural units constituting the base resin. The content ratio by percent is preferably 40 mol % or less, more preferably 35 mol % or less, and still more preferably 30 mol % or less.

[Structural Unit (IV)]

The base resin optionally has, as other structural units, a structural unit derived from hydroxystyrene or a structural unit having a phenolic hydroxy group (hereinafter, both are also collectively referred to as "structural unit (IV)"). The structural unit (IV) contributes to improvement of etching resistance and improvement of a difference in solubility of a developer (dissolution contrast) between an exposed area and an unexposed area. In particular, the resin can be suitably applied to pattern formation using exposure with radiation having a wavelength of 50 nm or less such as electron beam or EUV.

In this case, it is preferable to obtain the structural unit (IV) by polymerizing the monomer in a state where the phenolic hydroxyl group is protected by a protecting group such as an alkali-dissociable group during polymerization, and then deprotecting the polymerized product by hydrolysis. The structural unit which affords the structural unit (IV) by hydrolysis is preferably represented by the following formulas (4-1) and (4-2).

[Formula 11]

(4-1)

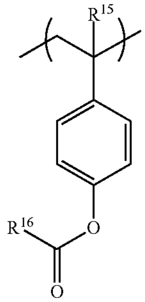

-continued (4-2)

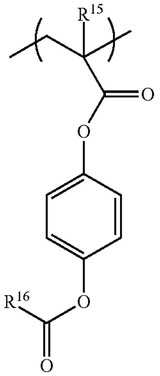

In the above formulas (4-1) and (4-2), $R^{15}$ is a hydrogen atom, a fluorine atom, a methyl group, or a trifluoromethyl group. $R^{16}$ is a monovalent hydrocarbon group having 1 to 20 carbon atoms or an alkoxy group. Examples of the monovalent hydrocarbon group having 1 to 20 carbon atoms as $R^{16}$ include monovalent hydrocarbon groups having 1 to 20 carbon atoms as $R^{12}$ in the structural unit (I). Examples of the alkoxy group include a methoxy group, an ethoxy group, and a tert-butoxy group.

As $R^{16}$, alkyl groups and alkoxy groups are preferable, and among them, a methyl group and a tert-butoxy group are more preferable.

In the case of a resin for exposure to radiation having a wavelength of 50 nm or less, the content ratio of the structural unit (IV) is preferably 10 mol % or more, and more preferably 20 mol % or more based on all structural units constituting the resin. The content ratio is preferably 70 mol % or less, and more preferably 60 mol % or less.

(Method for Synthesizing Base Resin)

The base resin can be synthesized by, for example, polymerizing monomers that will afford respective structural units in an appropriate solvent using a radical polymerization initiator or the like.

Examples of the radical polymerization initiator include azo radical initiators, such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile) and dimethyl 2,2'-azobisisobutyrate; and peroxide radical initiators, such as benzoyl peroxide, t-butyl hydroperoxide and cumene hydroperoxide. Among them, AIBN and dimethyl 2,2'-azobisisobutyrate are preferable, and AIBN is more preferable. These radical initiators can be used singly or in combination of two or more types thereof.

Examples of the solvent used in the polymerization include:

alkanes such as n-pentane, n-hexane, n-heptane, n-octane, n-nonane, and n-decane;

cycloalkanes such as cyclohexane, cycloheptane, cyclooctane, decalin, and norbornane;

aromatic hydrocarbons such as benzene, toluene, xylene, ethylbenzene, and cumene;

halogenated hydrocarbons such as chlorobutanes, bromohexanes, dichloroethanes, hexamethylene dibromide, and chlorobenzene;

saturated carboxylic acid esters such as ethyl acetate, n-butyl acetate, i-butyl acetate, and methyl propionate;

ketones such as acetone, methyl ethyl ketone, 4-methyl-2-pentanone, and 2-heptanone;

ethers such as tetrahydrofuran, dimethoxyethane, and diethoxyethane;

Examples thereof include alcohols such as methanol, ethanol, 1-propanol, 2-propanol, and 4-methyl-2-pentanol. The solvents to be used in the polymerization may be used singly or in combination of two or more types thereof.

The reaction temperature in the polymerization is usually 40 °C to 150 °C, and preferably 50 °C to 120 °C. The reaction time is usually 1 hour to 48 hours, and preferably 1 hour to 24 hours.

The molecular weight of the base resin is not particularly limited, and the weight average molecular weight (Mw) as determined by Gel Permeation Chromatography (GPC) relative to standard polystyrene is preferably 1,000 or more and 50,000 or less, more preferably 2,000 or more and 30,000 or less, still more preferably 3,000 or more and 15,000 or less, and particularly preferably 4,000 or more and 12,000 or less. When the Mw of the base resin is less than the lower limit, the heat resistance of the resulting resist film may be deteriorated. When the Mw of the base resin exceeds the above upper limit, the developability of the resist film may be deteriorated.

The ratio (Mw/Mn) of Mw to the number average molecular weight (Mn) of the base resin as determined by GPC relative to standard polystyrene is usually 1 or more and 5 or less, preferably 1 or more and 3 or less, and more preferably 1 or more and 2 or less.

The Mw and the Mn of a resin in the present description are values measured using gel permeation chromatography (GPC) under the following conditions.

GPC column: two G2000HXL, one G3000HXL, one G4000HXL (all manufactured by Tosoh Corporation)

Column temperature: 40 °C

Elution solvent: tetrahydrofuran

Flow rate: 1.0 mL/min

Sample concentration: 1.0% by mass

Amount of sample injected: 100 μL

Detector: differential refractometer

Standard substance: monodisperse polystyrene

The content ratio of the base resin is preferably 70% by mass or more, more preferably 80% by mass or more, and still more preferably 85% by mass based on the total solid content of the radiation-sensitive resin composition.

(Other Resins)

The radiation-sensitive resin composition of the present embodiment may contain a resin having a higher content rate by mass of fluorine atoms than the base resin as described above (hereinafter also referred as "high fluorine-containing resin") as other resin. When the radiation-sensitive resin composition contains the high fluorine-containing resin, the high fluorine-containing resin can be localized in the surface layer of a resist film compared to the base resin, and as a result, the water repellency of the surface of the resist film can be further enhanced in the case of immersion exposure.

The high fluorine-containing resin preferably has, for example, a structural unit represented by the following formula (5) (hereinafter also referred to as "structural unit (V)), and as necessary, may have the structural unit (I) or the structural unit (II) in the base resin.

[Formula 12]

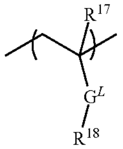

(5)

In the above formula (5), $R^{17}$ is a hydrogen atom, a methyl group, or a trifluoromethyl group. GL is a single bond, an oxygen atom, a sulfur atom, —COO—, —$SO_2$ONH—, —CONH—, or —OCONH—. $R^{18}$ is a monovalent fluorinated chain hydrocarbon group having 1 to 20 carbon atoms or a monovalent fluorinated alicyclic hydrocarbon group having 3 to 20 carbon atoms.

As $R^{17}$, a hydrogen atom and a methyl group are preferable from the viewpoint of the copolymerizability of a monomer that affords the structural unit (V), and a methyl group is more preferable.

As the GL, a single bond and —COO— are preferable from the viewpoint of the copolymerizability of a monomer that affords the structural unit (V), and —COO— is more preferable.

Examples of the monovalent fluorinated chain hydrocarbon group having 1 to 20 carbon atoms represented by $R^{18}$ include groups in which some or all of the hydrogen atoms in the linear or branched chain alkyl group having 1 to 20 carbon atoms are substituted with fluorine atoms.

Examples of the monovalent fluorinated alicyclic hydrocarbon group having 3 to 20 carbon atoms represented by $R^{18}$ include monovalent fluorinated alicyclic hydrocarbon groups having 3 to 20 carbon atoms in which some or all of the hydrogen atoms of a mono- or polycyclic hydrocarbon group are substituted with fluorine atoms.

As $R^{18}$, fluorinated chain hydrocarbon groups are preferable, fluorinated alkyl groups are more preferable, and 2,2,2-trifluoroethyl group, 1,1,1,3,3,3-hexafluoropropyl group, and 5,5,5-trifluoro-1,1-diethylpentyl group is still more preferable.

When the high fluorine-containing resin contains the structural unit (V), the content ratio of the structural unit (V) is preferably 30 mol % or more, more preferably 40 mol % or more, still more preferably 45 mol % or more, and particularly preferably 50 mol % or more based on all structural units constituting the high fluorine-containing resin. The content ratio is preferably 95 mol % or less, more preferably 90 mol % or less, and still more preferably 85 mol % or less. When the content ratio of the structural unit (V) is adjusted to within the above range, the content rate by mass of fluorine atoms in the high fluorine-containing resin can more appropriately be adjusted and the localization in the surface layer of a resist film can be further promoted, and as a result, the water repellency of the resist film at the time of immersion exposure can be further enhanced.

The high fluorine-containing resin may have a fluorine atom-containing structural unit represented by the following formula (f-1) (hereinafter also referred to as structural unit (VI)) in addition to the structural unit (V) or instead of the structural unit (V). When the high fluorine-containing resin has the structural unit (f-1), solubility in an alkaline developer is improved, and the occurrence of development defects can be suppressed.

[Formula 13]

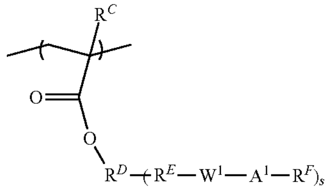

(f-1)

The structural unit (VI) is roughly divided into two cases: a case where it has (x) an alkali-soluble group, and a case where it has (y) a group that is dissociated by the action of an alkali to increase the solubility in an alkaline developer (hereinafter, also simply referred to as "alkali-dissociable group"). Commonly in (x) and (y), in the above formula (f-1), $R^C$ is a hydrogen atom, a fluorine atom, a methyl group, or a trifluoromethyl group. $R^D$ is a single bond, a hydrocarbon group having 1 to 20 carbon atoms with the valency of (s+1), a structure in which an oxygen atom, a sulfur atom, —$NR^{dd}$—, a carbonyl group, —COO— or —CONH— is connected to the terminal on $R^E$ side of the hydrocarbon group, or a structure in which some of the hydrogen atoms in the hydrocarbon group are substituted with organic groups having a hetero atom. $R^{dd}$ is a hydrogen atom or a monovalent hydrocarbon group having 1 to 10 carbon atoms. s is an integer of 1 to 3.

When the structural unit (VI) has (x) an alkali-soluble group, $R^F$ is a hydrogen atom, and $A^1$ is an oxygen atom, —COO—* or —$SO_2$O—*. * indicates a site that bonds to $R^F$. $W^1$ is a single bond, a hydrocarbon group having 1 to 20 carbon atoms, or a divalent fluorinated hydrocarbon group. When $A^1$ is an oxygen atom, $W^1$ is a fluorinated hydrocarbon group having a fluorine atom or a fluoroalkyl group on the carbon atom to which $A^1$ is bonded. $R^E$ is a single bond or a divalent organic group having 1 to 20 carbon atoms. When s is 2 or 3, a plurality of $R^E$'s, $W^1$'s, $A^1$'s, and $R^F$'s may be the same or different, respectively. When the structural unit (VI) has (x) an alkali-soluble group, affinity to an alkaline developer can be increased, and development defects can be suppressed. As the structural unit (VI) having (x) an alkali-soluble group, a case where $A^1$ is an oxygen atom and $W^1$ is a 1,1,1,3,3,3-hexafluoro-2,2-methanediyl group is particularly preferable.

When the structural unit (VI) has (y) an alkali-dissociable group, $R^F$ is a monovalent organic group having 1 to 30 carbon atoms, and $A^1$ is an oxygen atom, —$NR^{aa}$, —COO—* or —$SO_2$O—*. $R^{aa}$ is a hydrogen atom or a monovalent hydrocarbon group having 1 to 10 carbon atoms. * indicates a site that bonds to $R^F$. $W^1$ is a single bond or a divalent fluorinated hydrocarbon group having 1 to 20 carbon atoms. $R^E$ is a single bond or a divalent organic group having 1 to 20 carbon atoms. When $A^1$ is —COO—* or —$SO_2$O—*, $W^1$ or $R^F$ has a fluorine atom on a carbon atom bonded to $A^1$ or on a carbon atom adjacent thereto. When $A^1$ is an oxygen atom, $W^1$ and $R^E$ are single bonds, $R^D$ is a structure in which a carbonyl group is bonded to a terminal on the $R^E$ side of a hydrocarbon group having 1 to 20 carbon atoms, and $R^F$ is an organic group having a fluorine atom. When s is 2 or 3, a plurality of $R^E$'s, $W^1$'s, $A^1$'s, and $R^F$'s may be the same or different, respectively. When the structural unit (VI) has (y) an alkali-dissociable group, the surface of a resist film changes from hydrophobic to hydrophilic in an alkali development step. As a result, the affinity to a developer can be greatly increased, and development defects can be more efficiently suppressed. As the structural unit (VI) having (y) an alkali-dissociable group, a structural unit in which $A^1$ is —COO—*, and $R^F$, $W^1$, or both of them have a fluorine atom is particularly preferable.

As $R^C$, a hydrogen atom and a methyl group are preferable from the viewpoint of the copolymerizability of a monomer that affords the structural unit (VI), and a methyl group is more preferable.

When $R^E$ is a divalent organic group, a group having a lactone structure is preferable, a group having a polycyclic lactone structure is more preferable, and a group having a norbornanelactone structure is still more preferable.

When the high fluorine-containing resin contains the structural unit (VI), the content ratio of the structural unit (VI) is preferably 50 mol % or more, more preferably 60 mol % or more, and still more preferably 70 mol % or more based on all structural units constituting the high fluorine-containing resin. The content ratio is preferably 95 mol % or less, more preferably 90 mol % or less, and still more preferably 85 mol % or less. When the content ratio of the structural unit (VI) is set to fall within the above range, water repellency of a resist film during immersion exposure can further be improved.

[Other Structural Unit]

A high fluorine-containing resin may contain a structural unit having an alicyclic structure represented by the following formula (6) as a structural unit other than the structural units listed above,

[Formula 14]

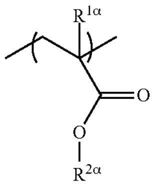

(6)

(In the above formula (6), $R^{1\alpha}$ represents a hydrogen atom, a fluorine atom, a methyl group, or a trifluoromethyl group. $R^{2\alpha}$ is a monovalent alicyclic hydrocarbon group having 3 to 20 carbon atoms.)

Examples of the monovalent alicyclic hydrocarbon group having 3 to 20 carbon atoms represented by $R^{2\alpha}$ in the above formula (6) include monovalent alicyclic hydrocarbon groups having 3 to 20 carbon atoms in which some or all of the hydrogen atoms of a mono- or polycyclic hydrocarbon group are substituted with fluorine atoms.

When the high fluorine-containing resin contains the structural unit having an alicyclic structure, the content ratio of the structural unit having an alicyclic structure is preferably 10 mol % or more, more preferably 20 mol % or more, and still more preferably 30 mol % or more based on all structural units constituting the high fluorine-content resin. The content ratio is preferably 70 mol % or less, more preferably 60 mol % or less, and still more preferably 50 mol % or less.

The lower limit of the Mw of the high fluorine-containing resin is preferably 1,000, more preferably 2,000, still more preferably 3,000, and particularly preferably 5,000. The upper limit of the Mw is preferably 50,000, more preferably 30,000, still more preferably 20,000, and particularly preferably 15,000.

The lower limit of the Mw/Mn of the high fluorine-containing resin is usually 1, and more preferably 1.1. The upper limit of the Mw/Mn is usually 5, preferably 3, more preferably 2, and still more preferably 1.9.

The content of the high fluorine-containing resin is preferably 0.1 parts by mass or more, more preferably 0.5 parts by mass or more, still more preferably 1 part by mass or more, and particularly preferably 1.5 parts by mass or more based on 100 parts by mass of the base resin. The content of the high fluorine-content resin is preferably 15 parts by mass or less, more preferably 12 parts by mass or less, still more preferably 10 parts by mass or less, and particularly preferably 8 parts by mass or less.

When the content of the high fluorine-containing resin is adjusted to within the above range, the high fluorine-containing resin can be more effectively localized in the surface layer of a resist film, and as a result, the water repellency of the surface of the resist film during immersion exposure can be further enhanced. The radiation-sensitive resin composition may contain one high fluorine-containing resin or two or more high fluorine-content resins.

(Method for Synthesizing High Fluorine-Containing Resin)

The high fluorine-containing resin can be synthesized by the same method as the method for synthesizing a base resin described above.

(Radiation-Sensitive Acid Generator)

The radiation-sensitive resin composition of the present embodiment further contains a radiation-sensitive acid generator that generates an acid by irradiation (exposure) with radiation. When the base resin having the structural unit (I) and the resin A contain the structural unit (2), the acid generated from the radiation-sensitive acid generator by exposure can dissociate the acid-dissociable groups of the structural unit (I) and the structural unit (2) to generate a carboxy group and the like.

When the radiation-sensitive resin composition contains the radiation-sensitive acid generator, the polarity of the resin in an exposed area increases, and as a result, when the developer is an aqueous alkaline solution, the resin in the exposed area is soluble in the developer, and on the other hand, when the developer is an organic solvent, the resin in the exposed area is hardly soluble in the developer.

Examples of the radiation-sensitive acid generator include an onium salt compound, a sulfonimide compound, a halogen-containing compound, and a diazoketone compound. Examples of the onium salt compound include a sulfonium salt, a tetrahydrothiophenium salt, an iodonium salt, a phosphonium salt, a diazonium salt, and a pyridinium salt. Among them, sulfonium salts and iodonium salts are preferable.

Examples of the acid generated during exposure include acids that generate sulfonic acid during exposure. Examples of such an acid include a compound in which the carbon atom adjacent to the sulfo group is substituted with one or more fluorine atoms or fluorinated hydrocarbon groups. Among them, as the radiation-sensitive acid generator, one having a cyclic structure is particularly preferable.

These radiation-sensitive acid generators may be used singly or two or more of them may be used in combination. The content of the radiation-sensitive acid generator (when a plurality of types of radiation-sensitive acid generators are used, their total content is taken) is preferably 0.1 parts by mass or more, more preferably 1 part by mass or more, and still more preferably 5 parts by mass or more based on 100 parts by mass of the base resin. The content is preferably 40 parts by mass or less, more preferably 35 parts by mass or less, still more preferably 30 parts by mass or less, and particularly preferably 20 parts by mass or less based on 100 parts by mass of the resin. As a result, superior sensitivity, LWR performance, and CDU performance can be exhibited at the time of resist pattern formation.

(Acid Diffusion Controlling Agent)

The radiation-sensitive resin composition may contain an acid diffusion controlling agent, as necessary. The acid diffusion controlling agent has the effect of controlling a phenomenon in which an acid generated from a radiation-sensitive acid generator by exposure diffuses in the resist film to suppress an undesired chemical reaction in an unexposed area. In addition, the storage stability of the resulting radiation-sensitive resin composition is improved. Furthermore, the resolution of a resist pattern is further improved, and it is possible to suppress a change in the line width of a resist pattern caused by a change in post-exposure delay that is the time between exposure and development, that is, it is possible to obtain a radiation-sensitive resin composition superior in process stability.

Examples of the acid diffusion controlling agent include a compound represented by the following formula (7) (hereinafter, also referred to as "nitrogen-containing compound (I)"), a compound having two nitrogen atoms in the same molecule (hereinafter, also referred to as "nitrogen-containing compound (II)"), a compound having three nitrogen atoms (hereinafter, also referred to as "nitrogen-containing compound (III)"), an amide group-containing compound, a urea compound, and a nitrogen-containing heterocyclic compound.

[Formula 15]

(7)

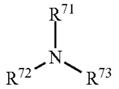

In the above formula (5), $R^{71}$, $R^{72}$, and $R^{73}$ each independently represent a hydrogen atom, a substituted or unsubstituted alkyl group, a substituted or unsubstituted cycloalkyl group, a substituted or unsubstituted aryl group, or a substituted or unsubstituted aralkyl group.

Examples of the nitrogen-containing compound (I) include monoalkylamines such as n-hexylamine; dialkylamines such as di-n-butylamine; trialkylamines such as triethylamine; and aromatic amines such as aniline.

Examples of the nitrogen-containing compound (II) include ethylenediamine and N,N,N',N'-tetramethylethylenediamine.

Examples of the nitrogen-containing compound (III) include polyamine compounds such as polyethyleneimine and polyallylamine; and polymers such as dimethylaminoethylacrylamide.

Examples of the amide group-containing compound include formamide, N-methylformamide, N,N-dimethylformamide, acetamide, N-methylacetamide, N,N-dimethylacetamide, propionamide, benzamide, pyrrolidone, and N-methylpyrrolidone.

Examples of the urea compound include urea, methylurea, 1,1-dimethylurea, 1,3-dimethylurea, 1,1,3,3-tetramethylurea, 1,3-diphenylurea, and tributylthiourea.

Examples of the nitrogen-containing heterocyclic compound include pyridines such as pyridine and 2-methylpyridine; morpholines such as N-propylmorpholine and N-(undecylcarbonyloxyethyl) morpholine; pyrazines, and pyrazoles.

As the nitrogen-containing organic compound, a compound having an acid-dissociable group can also be used. Examples of such a nitrogen-containing organic compound having an acid-dissociable group include N-t-butoxycarbonylpiperidine, N-t-butoxycarbonylimidazole, N-t-butoxycarbonylbenzimidazole, N-t-butoxycarbonyl-2-phenylbenzimidazole, N-(t-butoxycarbonyl) di-n-octylamine, N-(t-butoxycarbonyl) diethanolamine, N-(t-butoxycarbonyl) dicyclohexylamine, N-(t-butoxycarbonyl) diphenylamine, N-t-butoxycarbonyl-4-hydroxypiperidine, and N-t-amyloxycarbonyl-4-hydroxypiperidine.

As the acid diffusion controlling agent, a photodegradable base that generates a weak acid by exposure can be suitably used. Examples of the photodegradable base include a compound containing a radiation-sensitive onium cation decomposed by exposure and an anion of a weak acid. In the photodegradable base, a weak acid is generated from a proton generated by decomposition of a radiation-sensitive onium cation and an anion of the weak acid in an exposed area, so that acid diffusion controllability is deteriorated.

Examples of the photodegradable base include a sulfonium salt compound represented by the following formula (7-1) and an iodonium salt compound represented by the following formula (7-2).

[Formula 16]

$$J^{+}E^{-} \quad (7\text{-}1)$$

$$U^{+}Q^{-} \quad (7\text{-}2)$$

In the above formulas (7-1) and (7-2), $J^{+}$ is a sulfonium cation, and $U^{+}$ is an iodonium cation. Examples of the sulfonium cation represented by $J^{+}$ include a sulfonium cation represented by the following formula (X-1), and examples of the iodonium cation represented by $U^{+}$ include an iodonium cation represented by the following formula (X-2). E- and Q- each independently are an anion represented by OH—, Rα-COO—, or Rα-SO3-. Rα is an alkyl group, an aryl group, or an aralkyl group. The hydrogen atom of the aromatic ring of the aryl group or the aralkyl group represented by Rα may be substituted with a hydroxy group, a fluorine atom-substituted or unsubstituted alkyl group having 1 to 12 carbon atoms, or an alkoxy group having 1 to 12 carbon atoms.

[Formula 17]

(X-1)

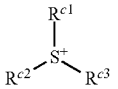

[Formula 18]

(X-2)

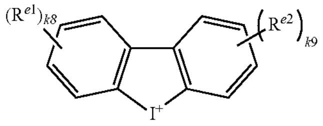

In the above formula (X-1), $R^{c1}$, $R^{c2}$, and $R^{c3}$ each independently are a substituted or unsubstituted linear or branched alkyl group having 1 to 12 carbon atoms, or a substituted or unsubstituted aromatic hydrocarbon group having 6 to 12 carbon atoms.

In the above formula (X-2), $R^{e1}$ and $R^{e2}$ each independently are a halogen atom, a substituted or unsubstituted linear or branched alkyl group having 1 to 12 carbon atoms, or a substituted or unsubstituted aromatic hydrocarbon group having 6 to 12 carbon atoms. k8 and k9 each independently are an integer of 0 to 4.

Examples of the substituent that may substitute a hydrogen atom of each of the groups include a halogen atom such as a fluorine atom, a chlorine atom, a bromine atom, or an iodine atom, a hydroxy group, a carboxy group, a cyano group, a nitro group, an alkyl group (when a hydrogen atom of a cycloalkyl group or an aromatic hydrocarbon group is substituted), an aryl group (when a hydrogen atom of an alkyl group is substituted), an alkoxy group, an alkoxycarbonyl group, an alkoxycarbonyloxy group, an acyl group, and an acyloxy group. Among them, a hydroxy group, an alkoxy group, an alkoxycarbonyl group, an alkoxycarbonyloxy group, an acyl group, and an acyloxy group are preferable, and an alkoxy group or an alkoxycarbonyl group is more preferable.

Examples of the photodegradable base include compounds represented by the following formulas.

[Formula 19]

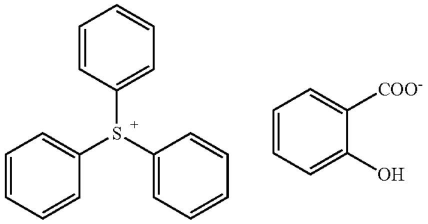

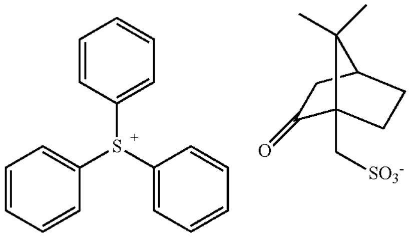

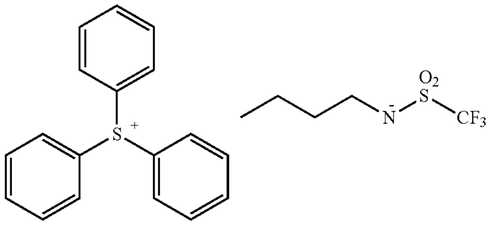

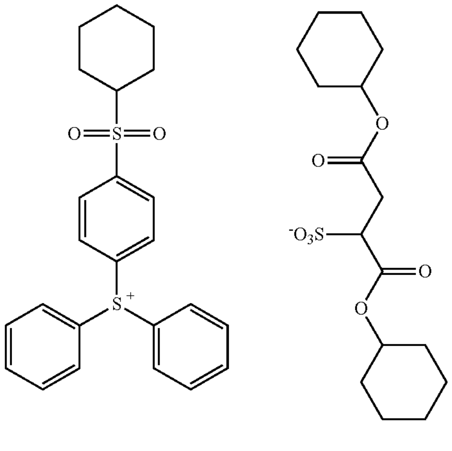

-continued

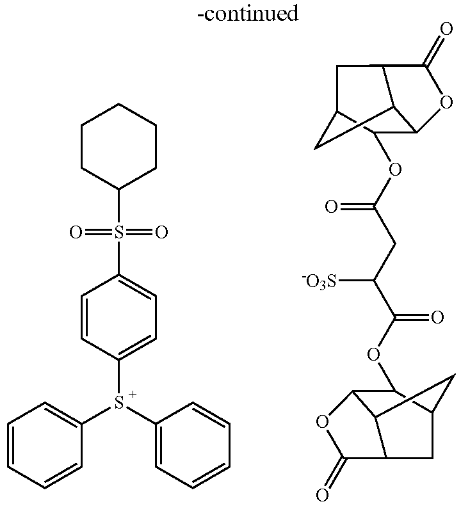

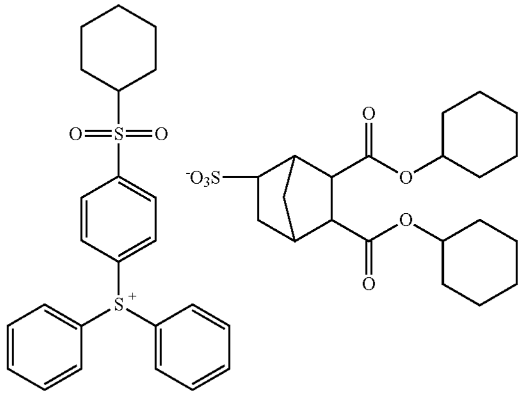

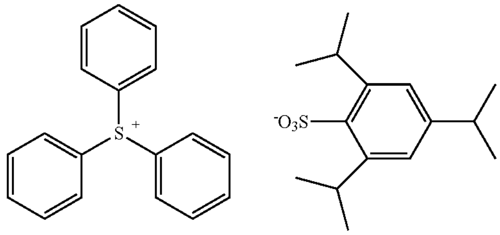

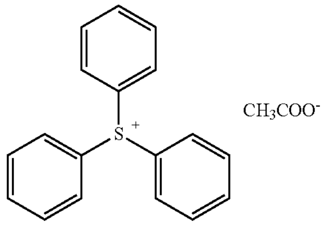

Among them, a sulfonium salt is preferable as the photodegradable base, a triarylsulfonium salt is more preferable, and triphenylsulfonium salicylate and triphenylsulfonium 10-camphorsulfonate are still more preferable.

These acid diffusion controlling agents may be used singly, or two or more thereof may be used in combination.

The content of the acid diffusion controlling agent is preferably 5 mol % or more, more preferably 10 mol % or more, and still more preferably 15 mol % or more based on the total number of moles of the radiation-sensitive acid generator. The content is preferably 40 mol % or less, more preferably 30 mol % or less, and still more preferably 25 mol % or less based on the total number of moles of the radiation-sensitive acid generator. When the content of the acid diffusion controlling agent is set to fall within the above range, the lithographic performance of the radiation-sensitive resin composition can further be improved.

(Solvent)

The radiation-sensitive resin composition according to the present embodiment contains a solvent. The solvent is not particularly limited as long as it is a solvent capable of dissolving or dispersing at least the resin having the structural unit (α), the acidic radiation-sensitive acid generator, and the like.

Examples of the solvent include an alcohol-based solvent, an ether-based solvent, a ketone-based solvent, an amide-based solvent, an ester-based solvent, and a hydrocarbon-based solvent.

Examples of the alcohol-based solvent include:

monoalcohol-based solvents having 1 to 18 carbon atoms, such as iso-propanol, 4-methyl-2-pentanol, 3-methoxybutanol, n-hexanol, 2-ethylhexanol, furfuryl alcohol, cyclohexanol, 3,3,5-trimethylcyclohexanol, and diacetone alcohol;

polyhydric alcohol-based solvents having 2 to 18 carbon atoms, such as ethylene glycol, 1,2-propylene glycol, 2-methyl-2,4-pentanediol, 2,5-hexanediol, diethylene glycol, dipropylene glycol, triethylene glycol, and tripropylene glycol; and partially etherized polyhydric alcohol-based solvents resulting from etherification of some of the hydroxy groups of the above-described polyhydric alcohol-based solvent.

Examples of the ether-based solvent include:

dialkyl ether-based solvents, such as diethyl ether, dipropyl ether, and dibutyl ether;

cyclic ether-based solvents, such as tetrahydrofuran and tetrahydropyran;

aromatic ring-containing ether-based solvents, such as diphenyl ether and anisole (methyl phenyl ether); and polyhydric alcohol ether-based solvents resulting from etherification of the hydroxy groups of the above-described polyhydric alcohol-based solvent.

Examples of the ketone-based solvent include chain ketone-based solvents, such as acetone, butanone, and methyl-iso-butyl ketone;

cyclic ketone-based solvents, such as cyclopentanone, cyclohexanone, and methylcyclohexanone; and 2,4-pentanedione, acetonylacetone, and acetophenone.

Examples of the amide-based solvent include cyclic amide-based solvents, such as N,N'-dimethylimidazolidinone and N-methylpyrrolidone; and cyclic amide-based solvents, such as N-methylformamide, N,N-dimethylformamide, N,N-diethylformamide, acetamide, N-methylacetamide, N,N-dimethylacetamide, and N-methylpropionamide.

Examples of the ester-based solvent include:

monocarboxylate ester-based solvents, such as n-butyl acetate and ethyl lactate;

partially etherized polyhydric alcohol acetate-based solvents, such as diethylene glycol mono-n-butyl ether acetate, propylene glycol monomethyl ether acetate, and dipropylene glycol monomethyl ether acetate;

lactone-based solvents, such as γ-butyrolactone and valerolactone;

carbonate-based solvents, such as diethyl carbonate, ethylene carbonate, and propylene carbonate; and polyhydric carboxylic acid diester-based solvents, such as propylene glycol diacetate, methoxy triglycol acetate, diethyl oxalate, ethyl acetoacetate, ethyl lactate, and diethyl phthalate.

Examples of the hydrocarbon-based solvent include:

aliphatic hydrocarbon-based solvents, such as n-hexane, cyclohexane, and methylcyclohexane; and aromatic hydrocarbon-based solvents, such as benzene, toluene, di-iso-propylbenzene, and n-amylnaphthalene.

Among them, ester-based solvents and ketone-based solvents are preferable, polyhydric alcohol partial ether acetate-based solvents, cyclic ketone-based solvents, and lactone-based solvents are more preferable, and propylene glycol monomethyl ether acetate, cyclohexanone, and γ-butyrolactone are still more preferable. The radiation-sensitive resin composition may contain one type or two or more types of solvent.

(Other Optional Components)

The radiation-sensitive resin composition of the present disclosure may contain other optional components in addition to the components described above. Examples of the other optional components include a crosslinking agent, a localization enhancing agent, a surfactant, an alicyclic backbone-containing compound, and a sensitizer. Such other optional components may be used singly or two or more types thereof may be used in combination.

(Acid Diffusion Controlling Agent)

The radiation-sensitive resin composition of the present disclosure may contain an acid diffusion controlling agent. The acid diffusion controlling agent has the effect of controlling a phenomenon in which an acid generated from a radiation-sensitive acid generator by exposure diffuses in the resist film to suppress an undesired chemical reaction in an unexposed area. In addition, the storage stability of the resulting radiation-sensitive resin composition is improved. Furthermore, the resolution of a resist pattern is further improved, and it is possible to suppress a change in the line width of a resist pattern caused by a change in post-exposure delay that is the time between exposure and development, that is, it is possible to obtain a radiation-sensitive resin composition superior in process stability.

(Crosslinking Agent)

The crosslinking agent is a compound having two or more functional groups, and causes a crosslinking reaction in the resin component by an acid catalytic reaction in a baking step after a one-shot exposure step to increase the molecular weight of the resin component, thereby decreasing the solubility of a pattern-exposed area in a developer. Examples of the functional group include a (meth)acryloyl group, a hydroxymethyl group, an alkoxymethyl group, an epoxy group, and a vinyl ether group.

(Localization Enhancing Agent)

The localization enhancing agent is an agent having an effect of localizing the high fluorine-containing resin on the surface of a resist film more effectively. By including the localization enhancing agent in the radiation-sensitive resin composition, the amount of the high fluorine-containing resin added can be reduced as compared with conventional cases. Therefore, the localization enhancing agent can further suppress the elution of the ingredients of the radiation-sensitive resin composition from a resist film to an immersion medium and carry out the immersion exposure at higher speed with a high-speed scan, while maintaining the lithography performance of the radiation-sensitive resin composition. Examples of a compound that can be used as the localization enhancing agent includes low molecular weight compounds having a specific dielectric constant of not less than 30 and not more than 200 and a boiling point of 100 °C or higher at 1 atm. Specific examples of such a compound include lactone compounds, carbonate compounds, nitrile compounds, and polyhydric alcohols.

Examples of the lactone compound include γ-butyrolactone, valerolactone, mevalonic lactone, and norbornane lactone.

Examples of the carbonate compound include propylene carbonate, ethylene carbonate, butylene carbonate, and vinylene carbonate.

Examples of the nitrile compound include succinonitrile.

Examples of the polyhydric alcohol include glycerin.

The content of the localization enhancing agent is preferably 10 parts by mass or more, more preferably 15 parts by mass or more, still more preferably 20 parts by mass or more, and yet still more preferably 25 parts by mass or more, based on 100 parts by mass of the total amount of the resin in the radiation-sensitive resin composition. The content of the localization enhancing agent is preferably 300 parts by mass or less, more preferably 200 parts by mass or less, still more preferably 100 parts by mass or less, and particularly preferably 80 parts by mass or less. The radiation-sensitive resin composition may contain one or two or more of localization enhancing agents.

(Surfactant)

The surfactant exerts the effect of improving coatability, striation, developability, and the like. Examples of the surfactant include nonionic surfactants, including polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, and polyethylene glycol distearate. Examples of a commercially available surfactant include KP341 (manufactured by Shin-Etsu Chemical Co., Ltd.), POLYFLOW No. 75, POLYFLOW No. 95 (both manufactured by Kyoeisha Chemical Co., Ltd.), EFTOP EF301, EFTOP EF303, EFTOP EF352 (all manufactured by Tohkem Products Corporation), MEGAFACE F171, MEGAFACE F173 (both manufactured by DIC), Fluorad FC430, Fluorad FC431 (both manufactured by Sumitomo 3M Limited), ASAHIGUARD AG710, SURFLON S-382, SURFLON SC-101, SURFLON SC-102, SURFLON SC-103, SURFLON SC-104, SURFLON SC-105, SURFLON SC-106 (all manufactured by Asahi Glass Co., Ltd.) The content of the surfactant in the radiation-sensitive resin composition is usually 2 parts by mass or less based on 100 parts by mass of the resin.

(Alicyclic Skeleton-Containing Compound)

The alicyclic skeleton-containing compound exerts the effect of improving dry etching resistance, the shape of a pattern, adhesiveness to a substrate, and the like.

Examples of the alicyclic skeleton-containing compound include:

- adamantane derivatives such as 1-adamantane carboxylic acid, 2-adamantanone, and t-butyl 1-adamantane carboxylic acid;
- deoxycholic acid esters such as t-butyl deoxycholate, t-butoxycarbonylmethyl deoxycholate, and 2-ethoxyethyl deoxycholate;
- lithocholic acid esters such as t-butyl lithocholate, t-butoxycarbonylmethyl lithocholate, and 2-ethoxyethyl lithocholate;
- 3-[2-hydroxy-2,2-bis(trifluoromethyl)ethyl]tetracyclo [4.4.0.1(2,5).1(7,10)]dodeca ne, and 2-hydroxy-9-methoxycarbonyl-5-oxo-4-oxa-tricyclo[4.2.1.0(3,7)] nonane. The content of the alicyclic skeleton-containing compound in the radiation-sensitive resin composition is usually 5 parts by mass or less based on 100 parts by mass of the resin.

(Sensitizer)

The sensitizer exhibits the action of increasing the amount of an acid generated from a radiation-sensitive acid generator or the like, and exerts the effect of improving the "apparent sensitivity" of the radiation-sensitive resin composition.

Examples of the sensitizer include carbazoles, acetophenones, benzophenones, naphthalenes, phenols, biacetyl, eosin, rose bengal, pyrenes, anthracenes, and phenothiazines. These sensitizers may be used singly or in combination of two or more of them. The content of the sensitizer in the radiation-sensitive resin composition is usually 2 parts by mass or less based on 100 parts by mass of the resin.

<Method for Preparing Radiation-Sensitive Resin Composition>

The radiation-sensitive resin composition can be prepared, for example, by mixing a resin having the structural unit (α), a radiation-sensitive acid generator, and as necessary, a high fluorine-containing resin, a solvent, and the like in a prescribed ratio. The radiation-sensitive resin composition is preferably filtered through, for example, a filter having a pore size of about 0.05 μm after mixing. The solid concentration of the radiation-sensitive resin composition is usually from 0.1% by mass to 50% by mass, preferably from 0.5% by mass to 30% by mass, and more preferably from 1% by mass to 20% by mass.

<Method for Forming Pattern>

The method for forming a resist pattern according to one embodiment of the present disclosure includes:

- step (1) of applying the radiation-sensitive resin composition directly or indirectly to a substrate to form a resist film (hereinafter also referred to as "resist film formation step"),
- step (2) of exposing the resist film to light (hereinafter also referred to as "exposure step"), and
- step (3) of developing the exposed resist film (hereinafter also referred to as "development step").

In accordance with this method for forming a resist pattern, a high-quality resist pattern can be formed because of the use of the radiation-sensitive resin composition superior in sensitivity, CDU performance, and pattern rectangularity in the exposure step. Hereinbelow, each of the steps will be described.

[Resist Film Forming Step]

In this step (step (1)), a resist film is formed from the radiation-sensitive resin composition. Examples of the substrate on which the resist film is formed include conventionally known substrates such as a silicon wafer, silicon dioxide, and a wafer coated with aluminum. An organic or inorganic antireflective film disclosed in, for example, JP-B-6-12452 or JP-A-59-93448 may be formed on the substrate. Examples of a method for applying the composition include spin coating, cast coating, and roll coating. After the application, prebaking (PB) may be performed to volatilize the solvent in the coating film, as necessary. The PB temperature is usually 60 °C to 140 °C, and preferably 80 °C to 120 °C. The PB time is usually 5 seconds to 600 seconds, and preferably 10 seconds to 300 seconds. The thickness of the resist film to be formed is preferably 10 nm to 1,000 nm, and more preferably 10 nm to 500 nm.

In the case of performing immersion exposure, regardless of the presence or absence of a water repellent polymer additive such as the high fluorine-containing resin in the radiation-sensitive resin composition, a protective film for immersion insoluble in an immersion liquid may be provided on the formed resist film for the purpose of avoiding direct contact between the immersion liquid and the resist film. As the protective film for immersion, either a solventremovable protective film that is to be removed by a solvent before the development step (see, for example, JP-A-2006-227632) or a developer-removable protective film that is to be removed simultaneously with the development in the development step (see, for example, WO 2005 069076 and WO 2006 035790) may be used. However, from the viewpoint of throughput, it is preferable to use a developer-removable protective film for immersion.

When the subsequent exposure step is performed with radiation having a wavelength of 50 nm or less, it is preferable to use a resin having the structural unit (I) and the structural unit (IV) as the base resin in the composition.

[Exposure Step]

In this step (the step (2)), the resist film formed in the resist film forming step, namely the step (1), is irradiated with radiation through a photomask (as the case may be, through an immersion medium such as water) to be exposed. Examples of the radiation to be used for the exposure include an electromagnetic wave including a visible ray, an ultraviolet ray, a far ultraviolet ray, an extreme ultraviolet ray (EUV), an X-ray, and a γ ray; an electron beam; and a charged particle radiation such as an a ray. Among them, far ultraviolet ray, electron beam, and EUV are preferable, ArF excimer laser light (wavelength: 193 nm), KrF excimer laser light (wavelength: 248 nm), electron beam, and EUV are more preferable, and an electron beam and EUV having a wavelength of 50 nm or less, which are positioned as next-generation exposure technology, are still more preferable.

When the exposure is performed by immersion exposure, examples of the immersion liquid to be used include water and a fluorine-based inert liquid. The immersion liquid is preferably a liquid that is transparent to an exposure wavelength and has a temperature coefficient of refractive index as small as possible to minimize the distortion of an optical image projected onto the film. Particularly, when an exposure light source is ArF excimer laser light (wavelength: 193 nm), water is preferably used from the viewpoint of availability and ease of handling in addition to the above-described viewpoints. When water is used, an additive that reduces the surface tension of water and increases the surface activity may be added in a small proportion. This additive is preferably one that does not dissolve the resist film on a wafer and has negligible influence on an optical coating at an under surface of a lens. The water to be used is preferably distilled water.

After the exposure, post exposure baking (PEB) is preferably carried out to promote the dissociation of the acid-dissociable group of the resin or the like due to the acid generated from the radiation-sensitive acid generator through the exposure in the exposed area of the resist film. As a result of the PEB, there is produced a difference in solubility in the developer between the exposed area and the unexposed area. The PEB temperature is usually 50 °C to 180 °C, and preferably 80 °C to 130 °C. The PEB time is usually 5 seconds to 600 seconds, and preferably 10 seconds to 300 seconds.

[Development Step]

In this step (the step (3)), the resist film exposed in the exposure step, namely the step (2), is developed. Thus, a prescribed resist pattern can be formed. In a common procedure, after the development, the film is washed with a rinsing liquid such as water or alcohol and dried.

Examples of the developer to be used for the development include, in the alkaline development, an alkaline aqueous solution obtained by dissolving at least one alkaline compound such as sodium hydroxide, potassium hydroxide, sodium carbonate, sodium silicate, sodium metasilicate, ammonia water, ethylamine, n-propylamine, diethylamine, di-n-propylamine, triethylamine, methyldiethylamine, ethyldimethylamine, triethanolamine, tetramethyl ammonium hydroxide (TMAH), pyrrole, piperidine, choline, 1,8-diazabicyclo-[5.4.0]-7-undecene, and 1,5-diazabicyclo-[4.3.0]-5-nonene. Among them, the aqueous TMAH solution is preferable, and a 2.38% by mass aqueous TMAH solution is more preferable.

In the case of organic solvent development, examples of the solvent include organic solvents such as hydrocarbon-based solvents, ether-based solvents, ester-based solvents, ketone-based solvents, and alcohol-based solvents, and solvents containing an organic solvent. Examples of the organic solvent include one type or two or more types of solvent among the solvents listed as the solvent for the radiation-sensitive resin composition. Among them, the ether-based solvent, the ester-based solvent, and the ketone-based solvent are preferable. As the ether-based solvent, glycol ether-based solvents are preferable, and ethylene glycol monomethyl ether and propylene glycol monomethyl ether are more preferable. As the ester-based solvents, acetate-based solvents are preferable, and n-butyl acetate and amyl acetate are more preferable. As the ketone-based solvents, chain ketones are preferable, and 2-heptanone is more preferable. The content of the organic solvent in the developer is preferably 80% by mass or more, more preferably 90% by mass or more, still more preferably 95% by mass or more, and particularly preferably 99% by mass or more. Examples of the components other than the organic solvent in the developer include water and silicon oil.

As described above, the developer may be either an alkaline developer or an organic solvent developer.

Examples of a development method include a method in which a substrate is immersed in a bath filled with a developer for a certain period of time (dipping method), a method in which a developer is allowed to be present on a surface of a substrate due to surface tension and to stand for a certain period of time (puddle method), a method in which a developer is sprayed onto a surface of a substrate (spray method), and a method in which a developer is discharged onto a substrate that is rotated at a constant speed while a developer discharge nozzle is scanned at a constant speed (dynamic dispensing method).

<Polymer (1)>

The polymer (1) of the present disclosure is a polymer having a structural unit represented by the following formula (1) (structural unit (α)).

[Formula 20]

(1)

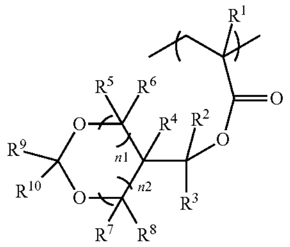

(In formula (1), $R^1$ is a hydrogen atom, a fluorine atom, a methyl group, or a trifluoromethyl group;

$R^2$ and $R^3$ each independently represent a monovalent hydrocarbon group having 1 to 10 carbon atoms or a divalent cyclic hydrocarbon group having 3 to 20 carbon atoms in which such groups are combined with each other and which is constituted of such groups together with the carbon atoms to which such groups are bonded;

$R^4$ is a hydrogen atom or a monovalent hydrocarbon group having 1 to 10 carbon atoms;

$R^5$ and $R^6$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded;

$R^7$ and $R^8$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded;

$R^9$ and $R^{10}$ each independently represent a monovalent organic group having 1 to 10 carbon atoms or a 3- to 30-membered divalent cyclic organic group in which such groups are combined with each other and which is constituted of such groups together with the carbon atoms to which such groups are bonded;

n1 is an integer of 1 to 4, and when n1 is 2 or more, a plurality of $R^5$ and $R^6$ are the same or different from each other; and n2 is an integer of 0 to 3, and when n2 is 2 or more, a plurality of $R^7$ and $R^8$ are the same or different from each other.)

The polymer (1) may be a resin having the structural unit (α) described above, and $R^1$ to $R^{10}$, and the like follow the description on the resin having the structural unit (α) described above, and the like.

<Compound (1)>

The compound (1) of the present disclosure is a compound represented by the following formula (3).

[Formula 21]

(3)

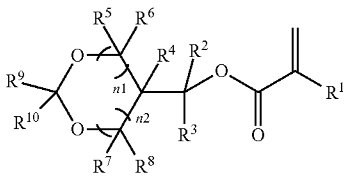

(In formula (1), $R^1$ is a hydrogen atom, a fluorine atom, a methyl group, or a trifluoromethyl group;

$R^2$ and $R^3$ each independently represent a monovalent hydrocarbon group having 1 to 10 carbon atoms or a divalent cyclic hydrocarbon group having 3 to 20 carbon atoms in which such groups are combined with each other and which is constituted of such groups together with the carbon atoms to which such groups are bonded;

$R^4$ is a hydrogen atom or a monovalent hydrocarbon group having 1 to 10 carbon atoms;

$R^5$ and $R^6$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded;

$R^7$ and $R^8$ each independently represent a hydrogen atom, a monovalent hydrocarbon group having 1 to 10 carbon atoms, or a divalent cyclic hydrocarbon group having 3 to 20 carbon atoms in which such groups are combined with each other and which is constituted of such groups together with the carbon atoms to which such groups are bonded;

$R^9$ and $R^{10}$ each independently represent a monovalent organic group having 1 to 10 carbon atoms or a 3- to 30-membered divalent cyclic organic group in which such groups are combined with each other and which is constituted of such groups together with the carbon atoms to which such groups are bonded;

n1 is an integer of 1 to 4, and when n1 is 2 or more, a plurality of $R^5$ and $R^6$ are the same or different from each other; and n2 is an integer of 0 to 3, and when n2 is 2 or more, a plurality of $R^7$ and $R^8$ are the same or different from each other.)

In the above formula (3), $R^1$ to $R^{10}$, n1, n2, and the like follow the description on the resin having the structural unit (α) described above, and the like.

Examples of the compound (1) include compounds represented by the following formulas (M-1) to (M-25).

[Formula 22]

(M-1)

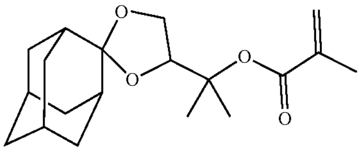

(M-2)

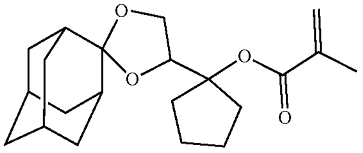

(M-3)

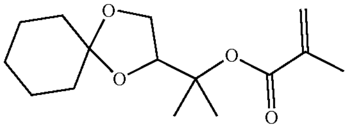

(M-4)

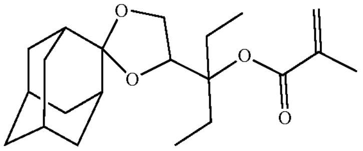

(M-5)

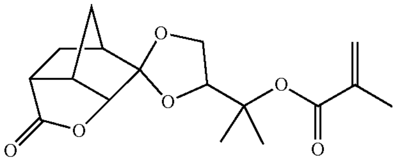

-continued
(M-6)
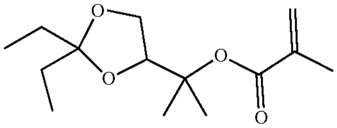
(M-7)
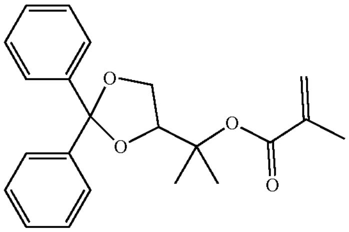
(M-8)
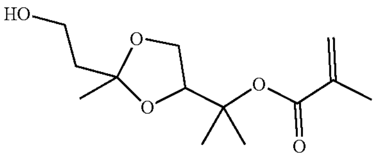
(M-9)
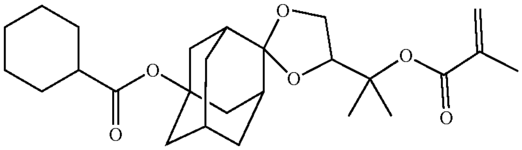
(M-10)
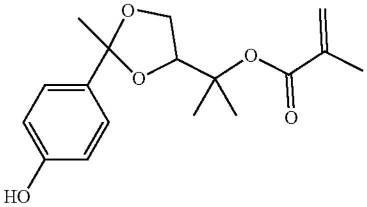
[Formula 23]
(M-11)
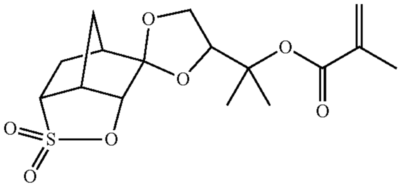
(M-12)
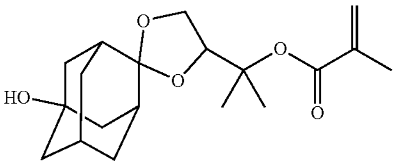
(M-13)
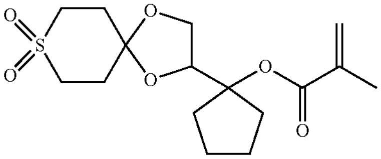
-continued
(M-14)
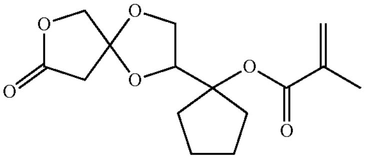
(M-15)
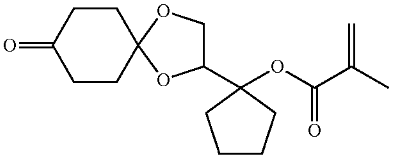
(M-16)
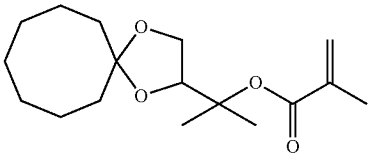
(M-17)
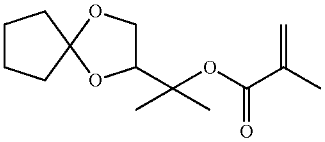
(M-18)
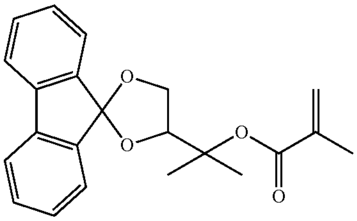
(M-19)
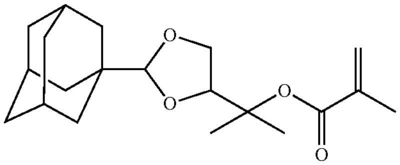
(M-20)
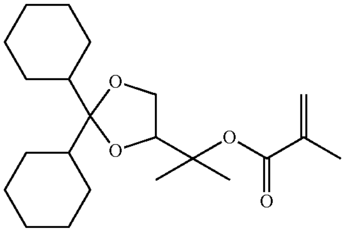
(M-21)
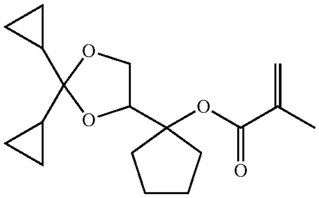

-continued (M-22)

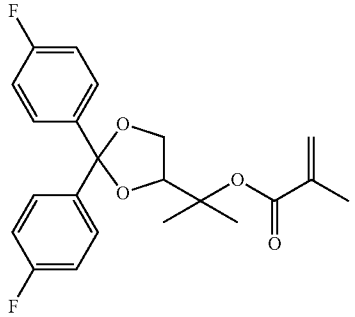

(M-23)

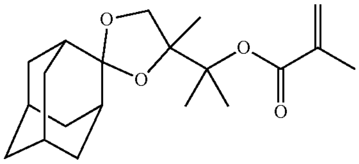

(M-24)

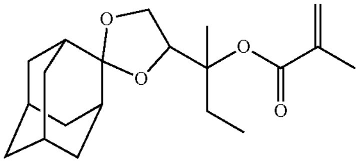

(M-25)

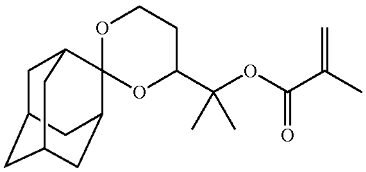

EXAMPLES

Hereinafter, the present invention will be specifically described with reference to Examples, but the present invention is not limited to these Examples. Methods for measuring various physical property values will be described below.

[Weight-Average Molecular Weight (Mw) and Number-Average Molecular Weight (Mn)]

The Mw and the Mn of polymers were measured by gel permeation chromatography (GPC) using GPC columns manufactured by Tosoh Corporation ("G2000HXL"×2, "G3000HXL"×1, "G4000HXL"×1) under the following conditions. A degree of dispersion (Mw/Mn) was calculated from results of the measured Mw and Mn.

Elution solvent: tetrahydrofuran

Flow rate: 1.0 mL/min

Sample concentration: 1.0% by mass

Amount of sample injected: 100 μL

Column temperature: 40 °C

Detector: differential refractometer

Standard substance: monodisperse polystyrene

[1H-NMR Analysis and 13C-NMR Analysis]

1H-NMR analysis and 13C-NMR analysis were performed using a nuclear magnetic resonance apparatus ("JNM-Delta 400" manufactured by JEOL Ltd.).

Synthesis of Compound (Monomer) [M]

[Synthesis Example 1] (Synthesis of Compound (M-1))

20.0 mmol of glyceric acid, 1.00 mmol of concentrated sulfuric acid, and 50 g of methanol were added into a reaction vessel, followed by stirring at 100 °C for 12 hours. Thereafter, a saturated aqueous solution of sodium bicarbonate was added to the stirred product to stop the reaction, and ethyl acetate was then added to resulting product to perform extraction, thereby separating an organic layer. The resulting organic layer was washed with a saturated aqueous solution of sodium chloride and then with water. After drying over sodium sulfate, a solvent was distilled off, and purification was performed by column chromatography to obtain an ester form in good yield.

20.0 mmol of 2-adamantanone, 1.00 mmol of concentrated sulfuric acid, and 50 g of toluene were added to the ester form, followed by stirring at 150 °C for 4 hours. Thereafter, a saturated aqueous solution of sodium bicarbonate was added to the stirred product to stop the reaction, and ethyl acetate was then added to resulting product to perform extraction, thereby separating an organic layer. The resulting organic layer was washed with a saturated aqueous solution of sodium chloride and then with water. After drying over sodium sulfate, a solvent was distilled off, and purification was performed by column chromatography to obtain an acetal form in good yield.

50 g of tetrahydrofuran was added to the acetal form and dissolved. After cooling the solution to 0 °C, 40.0 mmol of methylmagnesium iodide was added dropwise, and the mixture was stirred at room temperature for 5 hours. Thereafter, a saturated aqueous solution of ammonium chloride was added to the stirred product to stop the reaction, and ethyl acetate was then added thereto to perform extraction, thereby separating an organic layer. The resulting organic layer was washed with a saturated aqueous solution of sodium chloride and then with water. After drying over sodium sulfate, a solvent was distilled off, and purification was performed by column chromatography to obtain an alcohol form in good yield.

30.0 mmol of triethylamine, 4.00 mmol of 1,4-diazabicyclo[2.2.2]octane, and 70 g of acetonitrile were added to the alcohol form and dissolved. The solution was cooled to 0 °C, and 30.0 mmol of methacryloyl chloride was then added dropwise. After completion of the dropwise addition, the solution was stirred at room temperature for 6 hours. Thereafter, a saturated aqueous solution of ammonium chloride was added to the stirred product to stop the reaction, and ethyl acetate was then added thereto to perform extraction, thereby separating an organic layer. The resulting organic layer was washed with a saturated aqueous solution of sodium chloride and then with water. After drying over saturated sodium chloride, a solvent was distilled off, and purification was performed by column chromatography to obtain a monomer (M-1) in good yield. The synthesis scheme of the monomer (M-1) is shown below.

[Formula 24]

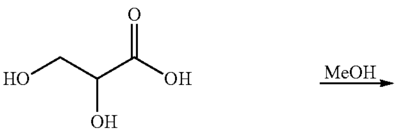

-continued

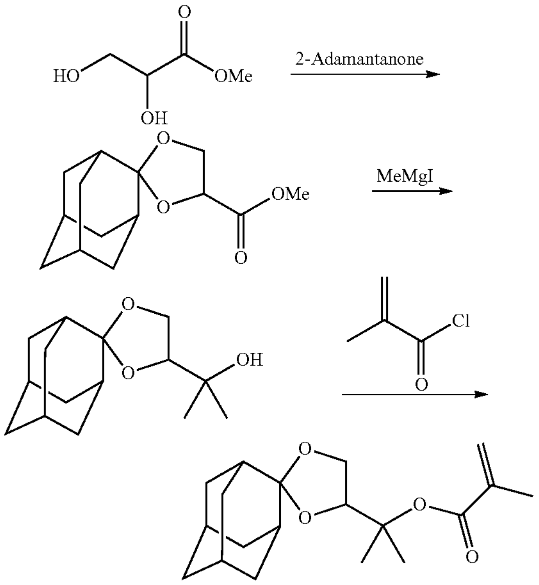

(M-1)

[Synthesis Examples 2 to 10] (Synthesis of Monomer (M-2) to Monomer (M-10))

Compounds represented by the following formulas (M-2) to (M-10) were synthesized in the same manner as in Synthesis Example 1 except that the raw materials and the precursor were appropriately changed. Hereinafter, the compounds represented by formulas (M-2) to (M-10) may be respectively referred to as "compound (M-2)" to "compound (M-10)" or "monomer (M-2)" to "monomer (M-10)".

[Formula 25]

(M-2)

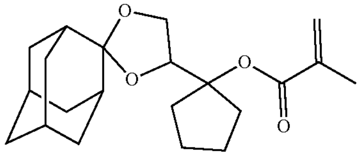

(M-3)

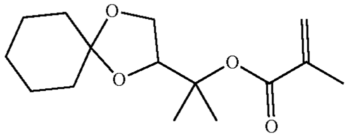

(M-4)

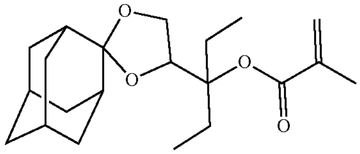

(M-5)

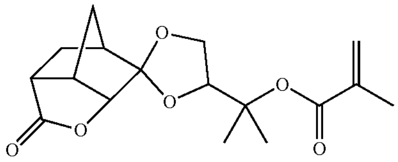

-continued (M-6)

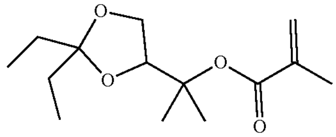

(M-7)

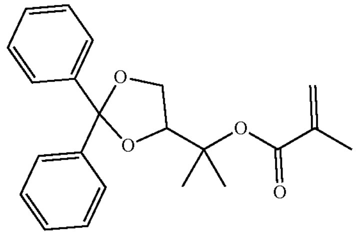

(M-8)

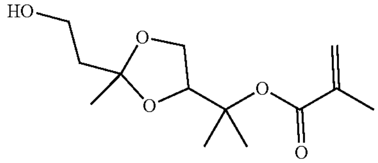

(M-9)

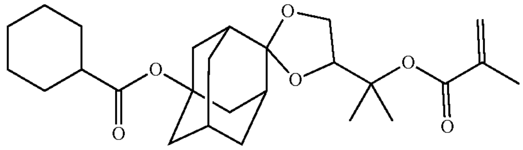

(M-10)

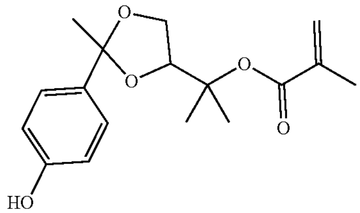

Synthesis of Polymer [A] and Polymer [E]

Among the monomers used in the synthesis of each polymer, monomers other than the monomer (M-1) to the monomer (M-10) are shown below. In the following synthesis examples, unless otherwise specified, "parts by mass" means a value taken when the total mass of the monomers used is 100 parts by mass, and "mol %" means a value taken when the total number of moles of the monomers used is 100 mol %. In addition, the present invention is not limited to the following structural units.

[Formula 26]

(m-1)

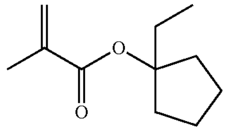

-continued
(m-2)
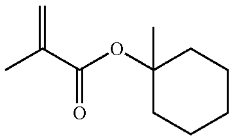
(m-3)
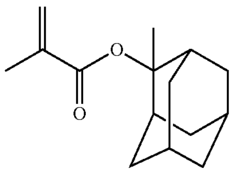
(m-4)
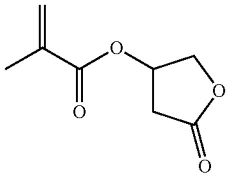
(m-5)
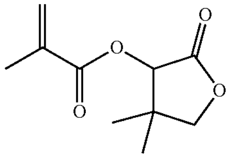
(m-6)
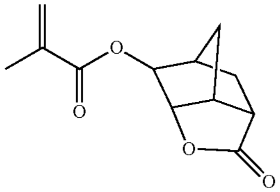
(m-7)
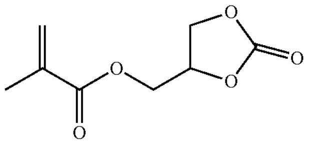
(m-8)
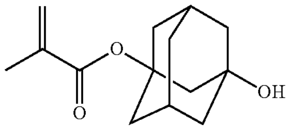
(m-9)
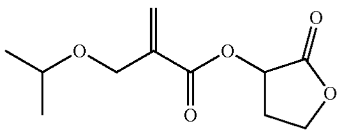
(m-10)
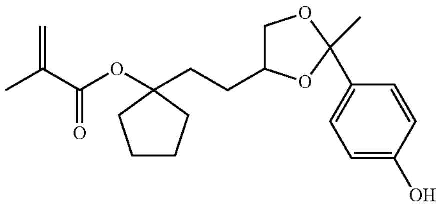
-continued
(m-11)
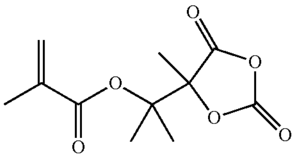
(m-12)
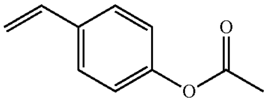
(m-13)
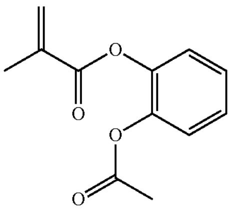
(m-14)
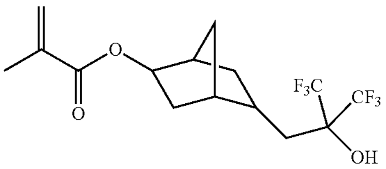
(m-15)
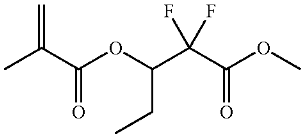
(m-16)
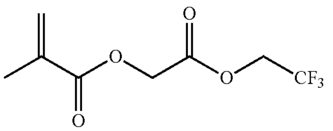
(m-17)
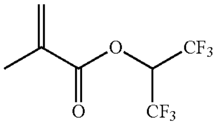
[Synthesis Example 1] (Synthesis of Polymer (A-1))
The monomer (M-1), a monomer (m-1), and a monomer (m-6) were dissolved at a molar ratio of 15/50/35 (mol %) in 2-butanone (200 parts by mass), and AIBN (azobisisobutyronitrile) (5 mol % based on 100 mol % in total of the monomers used) was added thereto as an initiator to prepare a monomer solution. 2-Butanone (100 parts by mass) was placed in an empty reaction vessel and purged with nitrogen for 30 minutes. Then, the temperature inside the reaction vessel was adjusted to 80 °C, and the monomer solution was added dropwise thereto over 3 hours with stirring. A polymerization reaction was performed for 6 hours with the start of the dropwise addition regarded as the start time of the polymerization reaction. After the completion of the polymerization reaction, the polymerization solution was cooled with water to 30 °C or lower. The polymerization solution cooled was poured into methanol (2,000 parts by mass), and a precipitated white powder was collected by filtration. The white powder collected was washed twice with methanol, collected by filtration, and dried at 50 °C for 10 hours, affording a white powdery polymer (A-1). The polymer (A-1) had an Mw of 6,170 and an Mw/Mn of 1.62. As a result of 13C-NMR analysis, the content ratios of the structural units derived from (M-1), (m-1), and (m-6) were respectively 15.6 mol %, 50.3 mol %, and 34.1 mol %.

Synthesis Examples 2 to 13 and Synthesis Examples 17 to 21

(Synthesis of Polymers (A-2) to (A-13) and (A-17) to (A-21))

Polymers (A-2) to (A-13) and (A-17) to (A-21) were synthesized in the same manner as in Synthesis Example 1 except that monomers of types and blending ratios shown in the following Table 1 were used. The content ratio (mol %) and physical property values (Mw and Mw/Mn) of each of the structural units of the resulting polymers are also shown in the following Table 1. In the following Table 1, "-" indicates that the corresponding monomer is not used.

TABLE 1

| | | Monomer that gives structural unit (M) | | | Monomer that gives structural unit (I) | | | Monomer that gives structural unit (II) | | | Monomer that gives structural unit (III) | | | | |
|---|---|---|---|---|---|---|---|---|---|---|---|---|---|---|---|
| | Polymer [A] | Type | Blending ratio (mol %) | Content of structural unit (mol %) | Type | Blending ratio (mol %) | Content of structural unit (mol %) | Type | Blending ratio (mol %) | Content of structural unit (mol %) | Type | Blending ratio (mol %) | Content of structural unit (mol %) | Mw | Mw/Mn |
| Synthesis Example 1 | A-1 | M-1 | 15 | 15.6 | m-1 | 50 | 50.3 | m-6 | 35 | 34.1 | — | — | — | 6170 | 1.62 |
| Synthesis Example 2 | A-2 | M-2 | 25 | 25.1 | m-2 | 25 | 25.5 | m-4<br>m-6 | 25<br>25 | 49.4 | — | — | — | 6520 | 1.57 |
| Synthesis Example 3 | A-3 | M-3 | 20 | 20.4 | m-1 | 25 | 25.4 | m-4 | 50 | 54.2 | — | — | — | 5800 | 1.63 |
| Synthesis Example 4 | A-4 | M-4 | 10 | 10.3 | m-1 | 50 | 50.2 | m-6<br>m-7 | 20<br>20 | 19.0<br>20.5 | — | — | — | 6350 | 1.7 |
| Synthesis Example 5 | A-5 | M-5 | 10 | 10.1 | m-1 | 30 | 30.4 | m-4 | 40 | 50.3 | m-8 | 10 | 9.2 | 6210 | 1.56 |
| Synthesis Example 6 | A-6 | M-6 | 10 | 10.2 | m-1 | 20 | 20.3 | m-4<br>m-7 | 50<br>10 | 60.6 | m-8 | 10 | 8.9 | 6820 | 1.71 |
| Synthesis Example 7 | A-7 | M-7 | 5 | 4.9 | m-1 | 35 | 35.3 | m-4<br>m-5 | 40<br>20 | 40.6<br>19.2 | — | — | — | 6880 | 1.66 |
| Synthesis Example 8 | A-8 | M-8 | 5 | 5.3 | m-1 | 45 | 45.7 | m-4 | 40 | 39.4 | m-8 | 10 | 9.6 | 6190 | 1.65 |
| Synthesis Example 9 | A-9 | M-9 | 15 | 14.3 | m-1 | 35 | 35.8 | m-5<br>m-6 | 20<br>30 | 20.5<br>29.4 | — | — | — | 6780 | 1.61 |
| Synthesis Example 10 | A-10 | M-10 | 20 | 19.7 | m-1 | 20 | 20.5 | m-4 | 40 | 40.5 | — | — | — | 6640 | 1.70 |
| Synthesis Example 11 | A-11 | M-1 | 5 | 5.2 | m-1<br>m-3 | 50<br>5 | 51.3<br>4.7 | m-9<br>m-6 | 10<br>30 | 9.1<br>29.7 | — | — | — | 6460 | 1.57 |
| Synthesis Example 12 | A-12 | M-2 | 5 | 4.9 | m-1<br>m-3 | 20<br>15 | 20.4<br>15.2 | m-4<br>m-5 | 40<br>20 | 40.1<br>19.4 | — | — | — | 7050 | 1.60 |
| Synthesis Example 13 | A-13 | M-3 | 5 | 5.4 | m-1<br>m-3 | 30<br>5 | 30.3<br>4.9 | m-6<br>m-7 | 30<br>30 | 28.9<br>30.5 | — | — | — | 6130 | 1.65 |

TABLE 2

| | | Monomer that gives structural unit (I) | | | Monomer that gives structural unit (II) | | | Monomer that gives structural unit (III) | | | | |
|---|---|---|---|---|---|---|---|---|---|---|---|---|
| | Polymer [A] | Type | Blending ratio (mol %) | Content of structural unit (mol %) | Type | Blending ratio (mol %) | Content of structural unit (mol %) | Type | Blending ratio (mol %) | Content of structural unit (mol %) | Mw | Mw/Mn |
| Synthesis Example 17 | A-17 | m-1<br>m-3 | 50<br>15 | 50.4<br>14.8 | m-6 | 35 | 34.8 | — | — | — | 6580 | 1.62 |
| Synthesis Example 18 | A-18 | m-1<br>m-2 | 20<br>10 | 20.1<br>10.3 | m-4<br>m-7 | 50<br>10 | 50.6<br>10.3 | m-8 | 10 | 8.7 | 6710 | 1.58 |
| Synthesis Example 19 | A-19 | m-1<br>m-3 | 50<br>10 | 50.2<br>9.7 | m-6<br>m-7 | 20<br>20 | 19.2<br>20.9 | — | — | — | 6920 | 1.65 |
| Synthesis Example 20 | A-20 | m-1 | 40 | 40.8 | m-7<br>m-10 | 30<br>30 | 30.5<br>28.7 | — | — | — | 7010 | 1.62 |
| Synthesis Example 21 | A-21 | m-1<br>m-3 | 50<br>10 | 51.4<br>9.4 | m-6<br>m-11 | 20<br>20 | 19.7<br>19.5 | — | — | — | 6890 | 1.69 |

[Synthesis Example 14] (Synthesis of Polymer (A-14))

The monomers (M-1), (in-1), (m-4), and (m-12) were dissolved in 1-methoxy-2-propanol (200 parts by mass with respect to all monomers) at a molar ratio of 5/35/20/40 (mol %). Next, AIBN (5 mol %) as an initiator was added to prepare a monomer solution. 1-methoxy-2-propanol (100 parts by mass with respect to all monomers) was placed in a reaction vessel, and the reaction vessel was purged with nitrogen for 30 minutes. Then, the temperature inside the reaction vessel was adjusted to 80 °C, and the monomer solution was added dropwise thereto over 3 hours with stirring. A polymerization reaction was performed for 6 hours with the start of the dropwise addition regarded as the start time of the polymerization reaction. After the completion of the polymerization reaction, the polymerization solution was cooled with water to 30 °C or lower. The cooled polymerization solution was charged into hexane (500 parts by mass based on the polymerization solution), and a precipitated white powder was separated by filtration. The white powder separated by filtration was washed with hexane twice, then separated by filtration, and dissolved in 1-methoxy-2-propanol (300 parts by mass). Next, methanol (500 parts by mass), triethylamine (50 parts by mass) and ultrapure water (10 parts by mass) were added, and a hydrolysis reaction was performed at 70 °C for 6 hours with stirring. After completion of the reaction, the remaining solvent was distilled off. The resulting solid was dissolved in acetone (100 parts by mass), and the solution was added dropwise to water (500 parts by mass) to solidify a resin. The resulting solid was separated by filtration, and dried at 50 °C for 13 hours to obtain a white powdery polymer (A-14) (yield: 72%). The polymer (A-14) had an Mw of 6,020 and an Mw/Mn of 1.61. As a result of 13C-NMR analysis, the content ratios of the structural units derived from (M-1), (m-1), (m-4), and (m-12) were respectively 5.2 mol %, 35.5 mol %, 19.2 mol %, and 40.1 mol %.

Synthesis Examples 15 to 16 and Synthesis Examples 22 to 23

(Synthesis of Polymers (A-15) to (A-16) and (A-22) to (A-23))

Polymers (A-15) to (A-16) and (A-22) to (A-23) were synthesized in the same manner as in Synthesis Example 14 except that monomers of types and blending ratios shown in the following Table 1 were used. The content ratio (mol %) and physical property values (Mw and Mw/Mn) of each of the structural units of the resulting polymers are also shown in the Table 1.

TABLE 3

| | | Monomer that gives structural unit (M) | | | Monomer that gives structural unit (I) | | | Monomer that gives structural unit (II) | | | Monomer that gives structural unit (IV) | | | | |
|---|---|---|---|---|---|---|---|---|---|---|---|---|---|---|---|
| | Polymer [A] | Type | Blending ratio (mol %) | Content of structural unit (mol %) | Type | Blending ratio (mol %) | Content of structural unit (mol %) | Type | Blending ratio (mol %) | Content of structural unit (mol %) | Type | Blending ratio (mol %) | Content of structural unit (mol %) | Mw | Mw/Mn |
| Synthesis Example 14 | A-14 | M-1 | 5 | 5.2 | m-1 | 35 | 35.5 | m-4 | 20 | 19.2 | m-12 | 40 | 40.1 | 6020 | 1.61 |
| Synthesis Example 15 | A-15 | M-1 | 5 | 5.4 | m-1 | 35 | 35.1 | m-6 | 20 | 19.7 | m-13 | 40 | 39.8 | 6400 | 1.57 |
| Synthesis Example 16 | A-16 | M-2 | 5 | 5.1 | m-1 | 35 | 35.3 | m-4 | 20 | 19.3 | m-12 | 40 | 40.3 | 7100 | 1.63 |

TABLE 4

| | | Monomer that gives structural unit (I) | | | Monomer that gives structural unit (II) | | | Monomer that gives structural unit (IV) | | | | |
|---|---|---|---|---|---|---|---|---|---|---|---|---|
| | Polymer [A] | Type | Blending ratio (mol %) | Content of structural unit (mol %) | Type | Blending ratio (mol %) | Content of structural unit (mol %) | Type | Blending ratio (mol %) | Content of structural unit (mol %) | Mw | Mw/Mn |
| Synthesis Example 22 | A-22 | m-1<br>m-3 | 35<br>5 | 35.5<br>4.8 | m-4 | 20 | 19.7 | m-12 | 40 | 40.0 | 6220 | 1.64 |
| Synthesis Example 23 | A-23 | m-1<br>m-3 | 35<br>5 | 35.9<br>4.6 | m-6 | 20 | 19.2 | m-13 | 40 | 40.3 | 6220 | 1.64 |

Synthesis of High Fluorine-Containing Polymer E

[Synthesis Example 32] (Synthesis of Polymer (E-1))

Monomers (m-1) and (m-15) were dissolved at a molar ratio of 20/80 (mol %) in 2-butanone (200 parts by mass), and AIBN (5 mol %) was added thereto as an initiator to prepare a monomer solution. 2-butanone (100 parts by mass) was placed in a reaction vessel, and then purged with nitrogen for 30 minutes. The temperature in the reaction vessel was adjusted to 80 °C, and the monomer solution was added dropwise thereto over 3 hours with stirring. A polymerization reaction was performed for 6 hours with the start of the dropwise addition regarded as the start time of the polymerization reaction. After the completion of the polymerization reaction, the polymerization solution was cooled with water to 30 °C or lower. The solvent was replaced with acetonitrile (400 parts by mass). Hexane (100 parts by mass) was then added, followed by stirring, and an acetonitrile layer was collected. The operation was repeated three times. By replacing the solvent with propylene glycol monomethyl ether acetate, a solution of the polymer (E-1) was obtained (yield: 83%). The polymer (E-1) had an Mw of 6,320 and an Mw/Mn of 1.67. As a result of 13C-NMR analysis, the content ratios of the structural units derived from (m-1) and (m-15) were respectively 19.7 mol % and 80.3 mol %.

[Synthesis Examples 33 to 35] (Synthesis of High Fluorine-Containing Resins (E-2) to (E-4))

High fluorine-containing resins (E-2) to (E-4) were synthesized in the same manner as in Synthesis Example 32 except that monomers of types and blending ratios shown in the following Table 5 were used. The content ratio (mol %) and physical property values (Mw and Mw/Mn) of each of the structural units of the resulting high fluorine-containing resins are also shown in the following Table 5.

<Preparation of Radiation-Sensitive Resin Composition>

The radiation-sensitive acid generating agents, the acid diffusion controlling agents, and the solvents constituting the radiation-sensitive resin compositions are described below.

[Acid Generating Agent [B]]

B-1 to B-5: Compounds represented by the following formulas (B-1) to (B-5).

[Formula 27]

(B-1)

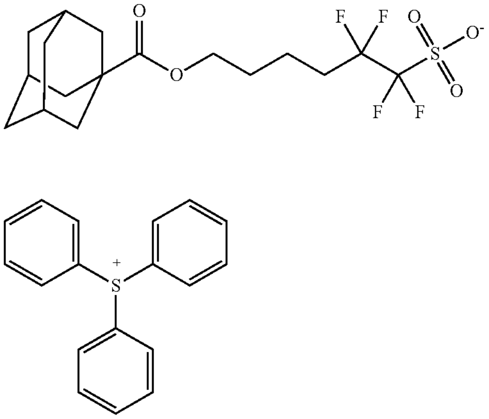

(B-2)

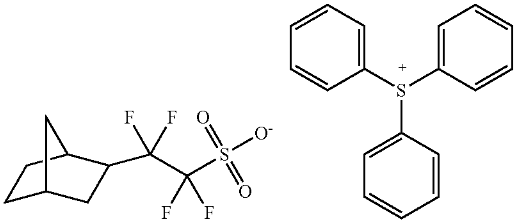

TABLE 5

| | Poly-mer [E] | Monomer that gives structural unit (F) Type | Blend-ing ratio (mol %) | Content of struc-tural unit (mol %) | Monomer that gives structural unit (I) Type | Blend-ing ratio (mol %) | Content of struc-tural unit (mol %) | Monomer that gives structural unit (III) Type | Blend-ing ratio (mol %) | Content of struc-tural unit (mol %) | Monomer that gives other structural unit Type | Blend-ing ratio (mol %) | Content of struc-tural unit (mol %) | Mw | Mw/Mn | Fluo-rine con-tent rate (%) |
|---|---|---|---|---|---|---|---|---|---|---|---|---|---|---|---|---|
| Synthesis Example 33 | E-2 | m-16 | 80 | 81.9 | m-1 | 20 | 18.1 | — | — | — | — | — | — | 7230 | 1.77 | 20.2 |
| Synthesis Example 34 | E-3 | m-17 | 60 | 58.8 | — | — | — | — | — | — | m-8 | 40 | 41.2 | 6530 | 1.81 | 29.0 |
| Synthesis Example 35 | E-4 | m-17 | 40 | 38.5 | m-3 | 10 | 9.3 | m-14 | 50 | 51.6 | — | — | — | 6910 | 1.76 | 35.1 |

-continued (B-3)

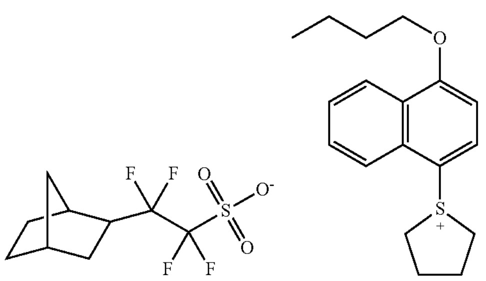

(B-4)

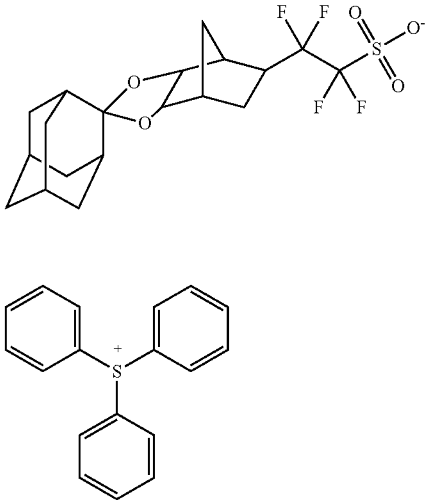

(B-5)

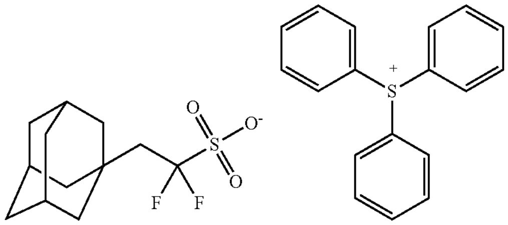

[Acid Diffusion Controlling Agent [C]]

C-1 to C-5: Compounds represented by the following formulas (C-1) to (C-5).

[Formula 28]

(C-1)

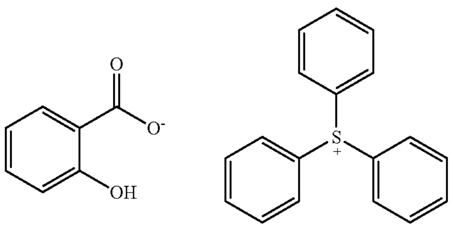

-continued (C-2)

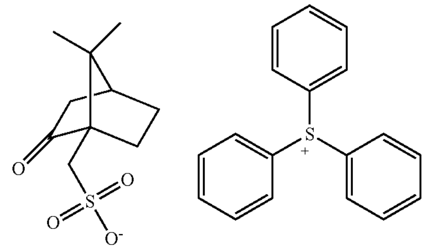

(C-3)

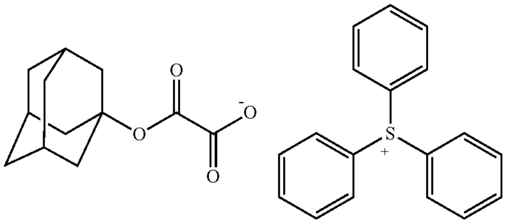

(C-4)

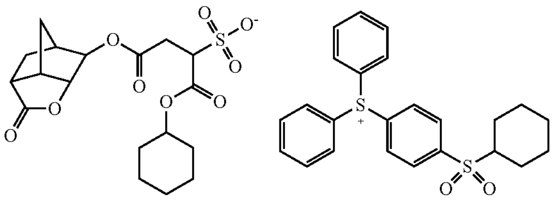

(C-5)

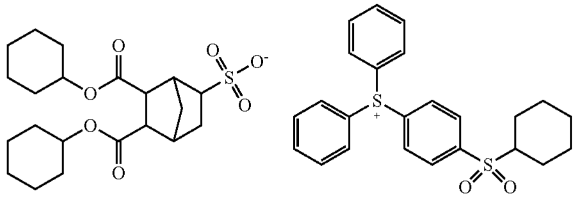

[Solvent [D]]

D-1: Propylene glycol monomethyl ether acetate

D-2: Cyclohexanone

D-3: γ-Butyrolactone

D-4: Ethyl lactate

[Preparation of Positive Radiation-Sensitive Resin Composition for ArF Exposure]

Example 1

100 parts by mass of (A-1) as the polymer [A], 12.0 parts by mass of (B-4) as the acid generator [B], 5.0 parts by mass of (C-1) as the acid diffusion controlling agent [C], 5.0 parts by mass (solid content) of (E-1) as the polymer [E], and 3,230 parts by mass of a mixed solvent of (D-1)/(D-2)/(D-3) as the solvent [D] were mixed, and the mixture was filtered through a membrane filter having a pore size of 0.2 μm to prepare a radiation-sensitive resin composition (J-1).

Examples 2 to 21 and Comparative Examples 1 to 5

Radiation-sensitive resin compositions (J-2) to (J-21), (J-35) to (J-37), and (CJ-1) to (CJ-5) were prepared in the same manner as in Example 1 except that the components of the types and contents shown in the following Table 6 were used.

TABLE 6

| | Radiation-sensitive resin composition | Polymer [A] Type | Polymer [A] Content (parts by mass) | Acid generating agent [B] Type | Acid generating agent [B] Content (parts by mass) | Acid diffusion controlling agent [C] Type | Acid diffusion controlling agent [C] Content (parts by mass) | Polymer [E] Type | Polymer [E] Content (parts by mass) | Organic solvent [D] Type | Organic solvent [D] Content (parts by mass) |
|---|---|---|---|---|---|---|---|---|---|---|---|
| Example 1 | J-1 | A-1 | 100 | B-4 | 12.0 | C-2 | 5.0 | E-1 | 5.0 | D-1/D-2/D-3 | 2240/960/30 |
| Example 2 | J-2 | A-2 | 100 | B-4 | 12.0 | C-2 | 5.0 | E-1 | 5.0 | D-1/D-2/D-3 | 2240/960/30 |
| Example 3 | J-3 | A-3 | 100 | B-4 | 12.0 | C-2 | 5.0 | E-1 | 5.0 | D-1/D-2/D-3 | 2240/960/30 |
| Example 4 | J-4 | A-4 | 100 | B-4 | 12.0 | C-2 | 5.0 | E-1 | 5.0 | D-1/D-2/D-3 | 2240/960/30 |
| Example 5 | J-5 | A-5 | 100 | B-4 | 12.0 | C-2 | 5.0 | E-1 | 5.0 | D-1/D-2/D-3 | 2240/960/30 |
| Example 6 | J-6 | A-6 | 100 | B-4 | 12.0 | C-2 | 5.0 | E-1 | 5.0 | D-1/D-2/D-3 | 2240/960/30 |
| Example 7 | J-7 | A-7 | 100 | B-4 | 12.0 | C-2 | 5.0 | E-1 | 5.0 | D-1/D-2/D-3 | 2240/960/30 |
| Example 8 | J-8 | A-8 | 100 | B-4 | 12.0 | C-2 | 5.0 | E-1 | 5.0 | D-1/D-2/D-3 | 2240/960/30 |
| Example 9 | J-9 | A-9 | 100 | B-4 | 12.0 | C-2 | 5.0 | E-1 | 5.0 | D-1/D-2/D-3 | 2240/960/30 |
| Example 10 | J-10 | A-10 | 100 | B-4 | 12.0 | C-2 | 5.0 | E-1 | 5.0 | D-1/D-2/D-3 | 2240/960/30 |
| Example 11 | J-11 | A-11 | 100 | B-4 | 12.0 | C-2 | 5.0 | E-1 | 5.0 | D-1/D-2/D-3 | 2240/960/30 |
| Example 12 | J-12 | A-12 | 100 | B-4 | 12.0 | C-2 | 5.0 | E-1 | 5.0 | D-1/D-2/D-3 | 2240/960/30 |
| Example 13 | J-13 | A-13 | 100 | B-4 | 12.0 | C-2 | 5.0 | E-1 | 5.0 | D-1/D-2/D-3 | 2240/960/30 |
| Example 14 | J-14 | A-1 | 100 | B-1 | 12.0 | C-2 | 5.0 | E-1 | 5.0 | D-1/D-2/D-3 | 2240/960/30 |
| Example 15 | J-15 | A-1 | 100 | B-2 | 12.0 | C-2 | 5.0 | E-1 | 5.0 | D-1/D-2/D-3 | 2240/960/30 |
| Example 16 | J-16 | A-1 | 100 | B-3 | 12.0 | C-2 | 5.0 | E-1 | 5.0 | D-1/D-2/D-3 | 2240/960/30 |
| Example 17 | J-17 | A-1 | 100 | B-5 | 12.0 | C-2 | 5.0 | E-1 | 5.0 | D-1/D-2/D-3 | 2240/960/30 |
| Example 18 | J-18 | A-1 | 100 | B-4 | 12.0 | C-1 | 5.0 | E-1 | 5.0 | D-1/D-2/D-3 | 2240/960/30 |
| Example 19 | J-19 | A-1 | 100 | B-4 | 12.0 | C-3 | 5.0 | E-1 | 5.0 | D-1/D-2/D-3 | 2240/960/30 |
| Example 20 | J-20 | A-1 | 100 | B-4 | 12.0 | C-4 | 5.0 | E-1 | 5.0 | D-1/D-2/D-3 | 2240/960/30 |
| Example 21 | J-21 | A-1 | 100 | B-4 | 12.0 | C-5 | 5.0 | E-1 | 5.0 | D-1/D-2/D-3 | 2240/960/30 |
| Example 35 | J-35 | A-1 | 100 | B-4 | 12.0 | C-2 | 5.0 | E-2 | 5.0 | D-1/D-2/D-3 | 2240/960/30 |
| Example 36 | J-36 | A-1 | 100 | B-4 | 12.0 | C-2 | 5.0 | E-3 | 5.0 | D-1/D-2/D-3 | 2240/960/30 |
| Example 37 | J-37 | A-1 | 100 | B-4 | 12.0 | C-2 | 5.0 | E-4 | 5.0 | D-1/D-2/D-3 | 2240/960/30 |
| Comparative Example 1 | CJ-1 | A-17 | 100 | B-4 | 12.0 | C-2 | 5.0 | E-1 | 5.0 | D-1/D-2/D-3 | 2240/960/30 |
| Comparative Example 2 | CJ-2 | A-18 | 100 | B-4 | 12.0 | C-2 | 5.0 | E-1 | 5.0 | D-1/D-2/D-3 | 2240/960/30 |
| Comparative Example 3 | CJ-3 | A-19 | 100 | B-4 | 12.0 | C-2 | 5.0 | E-1 | 5.0 | D-1/D-2/D-3 | 2240/960/30 |
| Comparative Example 4 | CJ-4 | A-20 | 100 | B-4 | 12.0 | C-2 | 5.0 | E-1 | 5.0 | D-1/D-2/D-3 | 2240/960/30 |
| Comparative Example 5 | CJ-5 | A-21 | 100 | B-4 | 12.0 | C-2 | 5.0 | E-1 | 5.0 | D-1/D-2/D-3 | 2240/960/30 |

<Formation of Resist Pattern Using Positive Radiation-Sensitive Resin Composition for ArF Exposure>

Onto the surface of a 12-inch silicon wafer, an underlayer antireflection film forming composition ("ARC66" manufactured by Brewer Science Incorporated.) was applied with use of a spin coater ("CLEAN TRACK ACT12" manufactured by Tokyo Electron Limited.). The wafer was then heated at 205 °C for 60 seconds to form an underlayer antireflection film having an average thickness of 105 nm. The positive radiation-sensitive resin composition for ArF exposure prepared above was applied onto the underlayer antireflection film with use of the spin coater, followed by performing PB (pre-baking) at 90 °C for 60 seconds. Thereafter, cooling was performed at 23 °C for 30 seconds to form a resist film having an average thickness of 90 nm. Next, this resist film was exposed through a mask pattern having a hole of 40 nm and a pitch of 86 nm using an ArF excimer laser immersion exposure apparatus ("TWINSCAN XT-1900i" manufactured by ASML) with NA of 1.35 under an optical condition of Annular ($\sigma$=0.8/0.6). After the exposure, PEB (post exposure baking) was performed at 90 °C for 60 seconds. Thereafter, the resist film was developed with an alkali with use of a 2.38% by mass aqueous TMAH solution as an alkaline developer, followed by washing with water and further drying to form a positive resist pattern (40-nm line-and-space pattern).

<Evaluation>

The resist pattern formed using the radiation-sensitive resin composition for ArF exposure was evaluated on sensitivity, LWR performance, and resist pattern shape according to the following methods. The results are shown in the following Table 7. It is to be noted that a scanning electron microscope ("CG-5000" manufactured by Hitachi High-Tech Corporation) was used for measurement of the resist pattern.

[Sensitivity]

An exposure dose at which a 40-nm line-and-space pattern was formed in the resist pattern formation using the radiation-sensitive resin composition for ArF exposure was defined as an optimum exposure dose (Eop), and this optimum exposure dose was defined as sensitivity (mJ/cm$^2$). The sensitivity was evaluated to be "good" in a case of being 25 mJ/cm$^2$ or less, and "poor" in a case of exceeding 25 mJ/cm$^2$.

[LWR Performance]

A resist pattern was formed by adjusting a mask size so as to form a 40-nm line-and-space pattern by irradiation with the optimum exposure dose obtained in the evaluation of the sensitivity. The formed resist pattern was observed from above the pattern with use of the scanning electron microscope. The variation in line width was measured at 500 points in total, the value of 3$\sigma$ was obtained from the distribution of the measured values, and the value of 3$\sigma$ was defined as LWR (nm). A smaller value of LWR indicates smaller roughness of the line and better performance. The LWR performance was evaluated as "good" when the LWR was 2.5 nm or less, and was evaluated as "poor" when the LWR exceeded 2.5 nm.

[Resist Pattern Shape]

The 40 nm line-and-space pattern formed by irradiation with the optimum exposure amount obtained in the evaluation of the sensitivity was observed using the scanning electron microscope, and the cross-sectional shape of the line-and-space pattern was evaluated. The rectangularity of the resist pattern was evaluated as "A" when the ratio of the length of a lower side to the length of an upper side in the cross-sectional shape was 1 or more and 1.05 or less, "B" when the ratio was more than 1.05 and 1.10 or less, and "C" when the ratio was more than 1.10.

TABLE 7

| | Radiation-sensitive resin composition | Sensitivity ($mJ/cm^2$) | LWR (nm) | Resist pattern shape |
|---|---|---|---|---|
| Example 1 | J-1 | 22 | 2.2 | A |
| Example 2 | J-2 | 20 | 2.3 | A |
| Example 3 | J-3 | 19 | 2.2 | A |
| Example 4 | J-4 | 21 | 2.0 | A |
| Example 5 | J-5 | 18 | 2.4 | A |
| Example 6 | J-6 | 15 | 2.3 | A |
| Example 7 | J-7 | 17 | 2.1 | A |
| Example 8 | J-8 | 19 | 2.4 | A |
| Example 9 | J-9 | 18 | 2.1 | A |
| Example 10 | J-10 | 20 | 2.3 | A |
| Example 11 | J-11 | 16 | 2.2 | A |
| Example 12 | J-12 | 17 | 2.2 | A |
| Example 13 | J-13 | 17 | 2.0 | A |
| Example 14 | J-14 | 19 | 2.4 | A |
| Example 15 | J-15 | 18 | 2.3 | A |
| Example 16 | J-16 | 21 | 1.9 | A |
| Example 17 | J-17 | 24 | 2.2 | A |
| Example 18 | J-18 | 23 | 2.1 | A |
| Example 19 | J-19 | 20 | 2.3 | A |
| Example 20 | J-20 | 23 | 2.5 | A |
| Example 21 | J-21 | 21 | 2.1 | A |
| Example 35 | J-35 | 21 | 2.2 | A |
| Example 36 | J-36 | 22 | 2.5 | A |
| Example 37 | J-37 | 21 | 2.3 | A |
| Comparative Example 1 | CJ-1 | 25 | 2.6 | B |
| Comparative Example 2 | CJ-2 | 26 | 2.9 | C |

TABLE 7-continued

| | Radiation-sensitive resin composition | Sensitivity ($mJ/cm^2$) | LWR (nm) | Resist pattern shape |
|---|---|---|---|---|
| Comparative Example 3 | CJ-3 | 28 | 3.1 | C |
| Comparative Example 4 | CJ-4 | 26 | 3.3 | C |
| Comparative Example 5 | CJ-5 | 32 | 3.8 | C |

As is apparent from the results in Table 7, the radiation-sensitive resin compositions of Examples were good in sensitivity, LWR performance, and resist pattern shape when used for ArF exposure, whereas the radiation-sensitive resin compositions of Comparative Examples were poorer in the characteristics than those of Examples. Therefore, when the radiation-sensitive resin compositions of Examples are used for ArF exposure, a resist pattern having high sensitivity, good LWR performance, and a good resist pattern shape can be formed.

[Preparation of Radiation-Sensitive Resin Composition for Extreme Ultraviolet Ray (EUV) Exposure]

Example 22

100 parts by mass of (A-14) as the polymer [A], 11.0 parts by mass of (B-4) as the acid generator [B], 5.0 parts by mass of (C-1) as the acid diffusion controlling agent [C], 5.0 parts by mass of (E-2) as the polymer [E], and 6,110 parts by mass of a mixed solvent of (D-1)/(D-4) as the solvent [D] were mixed, and the mixture was filtered through a membrane filter having a pore size of 0.2 μm to prepare a radiation-sensitive resin composition (J-22).

Examples 22 to 32 and Comparative Examples 6 to 7

Radiation-sensitive resin compositions (J-22) to (J-32) and (CJ-6) to (CJ-7) were prepared in the same manner as in Example 22 except that the components of the types and contents shown in the following Table 8 were used.

TABLE 8

| | Radiation- | Polymer [A] | | Acid generating agent [B] | | Acid diffusion controlling agent [C] | | Polymer [E] | | Organic solvent [D] | |
|---|---|---|---|---|---|---|---|---|---|---|---|
| | sensitive resin composition | Type | Content (parts by mass) | Type | Content (parts by mass) | Type | Content (parts by mass) | Type | Content (parts by mass) | Type | Content (parts by mass) |
| Example 22 | J-22 | A-14 | 100 | B-4 | 11.0 | C-1 | 5.0 | E-2 | 5.0 | D-1/D-4 | 4280/1830 |
| Example 23 | J-23 | A-15 | 100 | B-4 | 11.0 | C-1 | 5.0 | E-2 | 5.0 | D-1/D-4 | 4280/1830 |
| Example 24 | J-24 | A-16 | 100 | B-4 | 11.0 | C-1 | 5.0 | E-2 | 5.0 | D-1/D-4 | 4280/1830 |
| Example 25 | J-25 | A-14 | 100 | B-1 | 11.0 | C-1 | 5.0 | E-2 | 5.0 | D-1/D-4 | 4280/1830 |
| Example 26 | J-26 | A-14 | 100 | B-2 | 11.0 | C-1 | 5.0 | E-2 | 5.0 | D-1/D-4 | 4280/1830 |
| Example 27 | J-27 | A-14 | 100 | B-3 | 11.0 | C-1 | 5.0 | E-2 | 5.0 | D-1/D-4 | 4280/1830 |
| Example 28 | J-28 | A-14 | 100 | B-5 | 11.0 | C-1 | 5.0 | E-2 | 5.0 | D-1/D-4 | 4280/1830 |
| Example 29 | J-29 | A-14 | 100 | B-4 | 11.0 | C-2 | 5.0 | E-2 | 5.0 | D-1/D-4 | 4280/1830 |
| Example 30 | J-30 | A-14 | 100 | B-4 | 11.0 | C-3 | 5.0 | E-2 | 5.0 | D-1/D-4 | 4280/1830 |
| Example 31 | J-31 | A-14 | 100 | B-4 | 11.0 | C-4 | 5.0 | E-2 | 5.0 | D-1/D-4 | 4280/1830 |
| Example 32 | J-32 | A-14 | 100 | B-4 | 11.0 | C-5 | 5.0 | E-2 | 5.0 | D-1/D-4 | 4280/1830 |
| Comparative Example 6 | CJ-4 | A-22 | 100 | B-4 | 11.0 | C-1 | 5.0 | E-2 | 5.0 | D-1/D-4 | 4280/1830 |
| Comparative Example 7 | CJ-5 | A-23 | 100 | B-4 | 11.0 | C-1 | 5.0 | E-2 | 5.0 | D-1/D-4 | 4280/1830 |

<Formation of Resist Pattern Using Radiation-Sensitive Resin Composition for EUV Exposure>

Onto the surface of a 12-inch silicon wafer, an underlayer antireflection film forming composition ("ARC66" manufactured by Brewer Science Incorporated.) was applied with use of a spin coater ("CLEAN TRACK ACT12" manufactured by Tokyo Electron Limited.). The wafer was then heated at 205 °C for 60 seconds to form an underlayer antireflection film having an average thickness of 105 nm. The radiation-sensitive resin composition for EUV exposure prepared above was applied onto the underlayer antireflection film with use of the spin coater, followed by performing PB at 130 °C for 60 seconds. Thereafter, cooling was performed at 23 °C for 30 seconds to form a resist film having an average thickness of 55 nm. Next, the resist film was exposed by an EUV exposure apparatus ("NXE3300", manufactured by ASML) with NA of 0.33 under a lighting condition of Conventional s=0.89 and with a mask of imecDEFECT32FFR02. After exposing, PEB was performed at 120 °C for 60 seconds. Thereafter, the resist film was developed with an alkali with use of a 2.38% by mass aqueous TMAH solution as an alkaline developer, followed by washing with water and further drying to form a positive resist pattern (32-nm line-and-space pattern).

<Evaluation>

The resist patterns formed using the radiation-sensitive resin compositions for EUV exposure were evaluated on sensitivity and LWR performance according to the following methods. The results are shown in the following Table 5. It is to be noted that a scanning electron microscope ("CG-5000" manufactured by Hitachi High-Tech Corporation) was used for measurement of the resist pattern.

[Sensitivity]

An exposure dose at which a 32-nm line-and-space pattern was formed in the aforementioned resist pattern formation using the radiation-sensitive resin composition for EUV exposure was defined as an optimum exposure dose, and this optimum exposure dose was defined as sensitivity ($mJ/cm^2$). The sensitivity was evaluated to be "good" in a case of being 25 $mJ/cm^2$ or less, and "poor" in a case of exceeding 25 $mJ/cm^2$.

[LWR Performance]

A resist pattern was formed by adjusting a mask size so as to form a 32-nm line-and-space pattern by irradiation with the optimum exposure dose obtained in the evaluation of the sensitivity. The formed resist pattern was observed from above the pattern with use of the scanning electron microscope. The variation in line width was measured at 500 points in total, the value of $3\sigma$ was obtained from the distribution of the measured values, and the value of $3\sigma$ was defined as LWR (nm). The smaller the value of the LWR is, the smaller the wobble of the line is, which is better. The LWR performance was evaluated as "good" when the LWR was 2.5 nm or less, and was evaluated as "poor" when the LWR exceeded 2.5 nm.

[Resist Pattern Shape]

The 40 nm line-and-space pattern formed by irradiation with the optimum exposure amount obtained in the evaluation of the sensitivity was observed using the scanning electron microscope, and the cross-sectional shape of the line-and-space pattern was evaluated. The rectangularity of the resist pattern was evaluated as "A" when the ratio of the length of a lower side to the length of an upper side in the cross-sectional shape was 1 or more and 1.05 or less, "B" when the ratio was more than 1.05 and 1.10 or less, and "C" when the ratio was more than 1.10.

TABLE 9

| | Radiation-sensitive resin composition | Sensitivity ($mJ/cm^2$) | LWR (nm) | Resist pattern shape |
|---|---|---|---|---|
| Example 22 | J-22 | 20 | 2.0 | A |
| Example 23 | J-23 | 24 | 2.3 | A |
| Example 24 | J-24 | 22 | 2.1 | A |
| Example 25 | J-25 | 16 | 2.5 | A |
| Example 26 | J-26 | 18 | 2.2 | A |
| Example 27 | J-27 | 18 | 2.0 | A |
| Example 28 | J-28 | 19 | 2.1 | A |
| Example 29 | J-29 | 24 | 2.4 | A |
| Example 30 | J-30 | 22 | 2.1 | A |
| Example 31 | J-31 | 21 | 2.3 | A |
| Example 32 | J-32 | 22 | 2.3 | A |
| Comparative Example 6 | CJ-4 | 26 | 3.3 | C |
| Comparative Example 7 | CJ-5 | 29 | 3.4 | C |

As is apparent from the results in Table 8, the radiation-sensitive resin compositions of Examples were good in sensitivity, LWR performance, and resist pattern shape when used for EUV exposure, whereas the radiation-sensitive resin compositions of Comparative Examples were poorer in the characteristics than those of Examples.

[Preparation of Negative Radiation-Sensitive Resin Composition for ArF Exposure, and Formation and Evaluation of Resist Pattern Using this Composition]

Example 33

100 parts by mass of (A-2) as the polymer [A], 12.0 parts by mass of (B-1) as the acid generator [B], 5.0 parts by mass of (C-1) as the acid diffusion controlling agent [C], 5.0 parts by mass (solid content) of (E-3) as the polymer [E], and 3,230 parts by mass of a mixed solvent of (D-1)/(D-2)/(D-3) as the solvent [D] were mixed, and the mixture was filtered through a membrane filter having a pore size of 0.2 μm to prepare a radiation-sensitive resin composition (J-33).

Onto the surface of a 12-inch silicon wafer, an underlayer antireflection film forming composition ("ARC66" manufactured by Brewer Science Incorporated.) was applied with use of a spin coater ("CLEAN TRACK ACT12" manufactured by Tokyo Electron Limited.). The wafer was then heated at 205 °C for 60 seconds to form an underlayer antireflection film having an average thickness of 105 nm. The negative radiation-sensitive resin composition for ArF exposure (J-33) prepared above was applied onto the underlayer antireflection film with use of the spin coater, followed by performing PB (pre-baking) at 90 °C for 60 seconds. Thereafter, cooling was performed at 23 °C for 30 seconds to form a resist film having an average thickness of 90 nm. Next, this resist film was exposed through a mask pattern having a hole of 39 nm and a pitch of 86 nm using an ArF excimer laser immersion exposure apparatus ("TWINSCAN XT-1900i" manufactured by ASML) with NA of 1.35 under an optical condition of Annular ($\sigma$=0.8/0.6). After the exposure, PEB (post exposure baking) was performed at 90 °C for 60 seconds. Thereafter, the resist film was developed with an organic solvent using n-butyl acetate as an organic solvent developer, and dried to form a negative resist pattern (39 nm line-and-space pattern).

The resist pattern using the negative radiation-sensitive resin composition for ArF exposure was evaluated in the same manner as in the evaluation of the resist pattern using the positive radiation-sensitive resin composition for ArF exposure. As a result, the radiation-sensitive resin composition of Example 33 had good sensitivity, LWR performance, and resist pattern shape even when a negative resist pattern was formed by ArF exposure.

[Preparation of Negative Radiation-Sensitive Resin Composition for EUV Exposure, and Formation and Evaluation of Resist Pattern Using this Composition]

Example 34

100 parts by mass of (A-14) as the polymer [A], 11.0 parts by mass of (B-2) as the acid generator [B], 5.0 parts by mass of (C-1) as the acid diffusion controlling agent [C], 5.0 parts by mass of (E-4) as the polymer [E], and 6,110 parts by mass of a mixed solvent of (D-1)/(D-4) as the solvent [D] were mixed, and the mixture was filtered through a membrane filter having a pore size of 0.2 μm to prepare a radiation-sensitive resin composition (J-34).

Onto the surface of a 12-inch silicon wafer, an underlayer antireflection film forming composition ("ARC66" manufactured by Brewer Science Incorporated.) was applied with use of a spin coater ("CLEAN TRACK ACT12" manufactured by Tokyo Electron Limited.). The wafer was then heated at 205 °C for 60 seconds to form an underlayer antireflection film having an average thickness of 105 nm. The radiation-sensitive resin composition for EUV exposure (J-34) prepared above was applied onto the underlayer antireflection film with use of the spin coater, followed by performing PB at 130 °C for 60 seconds. Thereafter, cooling was performed at 23 °C for 30 seconds to form a resist film having an average thickness of 55 nm. Next, the resist film was exposed by an EUV exposure apparatus ("NXE3300", manufactured by ASML) with NA of 0.33 under a lighting condition of Conventional s=0.89 and with a mask of imecDEFECT32FFR02. After exposing, PEB was performed at 120 °C for 60 seconds. Thereafter, the resist film was developed with an organic solvent using n-butyl acetate as an organic solvent developer, and dried to form a negative resist pattern (32 nm line-and-space pattern).

The resist pattern using the negative radiation-sensitive resin composition for EUV exposure was evaluated in the same manner as in the evaluation of the resist pattern using the positive radiation-sensitive resin composition for EUV exposure. As a result, the radiation-sensitive resin composition of Example 34 had good sensitivity, LWR performance, and resist pattern shape even when a negative resist pattern was formed by EUV exposure.

According to the radiation-sensitive resin composition and the method for forming a resist pattern of the present disclosure, a resist pattern having good sensitivity to exposure and excellent LWR performance and resist pattern shape can be formed. The polymer of the present disclosure can be suitably used as a polymer component of the radiation-sensitive resin composition. Since the compound of the present disclosure can be suitably used as a monomer component of the polymer, the compound can be suitably used in a processing process of a semiconductor device in which miniaturization is expected to further progress in the future.

Obviously, numerous modifications and variations of the present invention(s) are possible in light of the above teachings. It is therefore to be understood that within the scope of the appended claims, the invention(s) may be practiced otherwise than as specifically described herein.

What is claimed is:

1. A radiation-sensitive resin composition comprising:

a resin comprising a structural unit represented by formula (1);

a radiation-sensitive acid generator; and a solvent, (1)

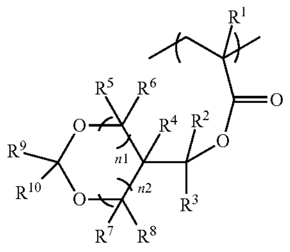

wherein in formula (1), $R^1$ is a hydrogen atom, a fluorine atom, a methyl group, or a trifluoromethyl group;

$R^2$ and $R^3$ each independently represent a monovalent hydrocarbon group having 1 to 10 carbon atoms, or taken together represent a divalent cyclic hydrocarbon group having 3 to 20 carbon atoms together with the carbon atom to which $R^2$ and $R^3$ are bonded;

$R^4$ is a hydrogen atom or a monovalent hydrocarbon group having 1 to 10 carbon atoms;

$R^5$ and $R^6$ each independently represent a hydrogen atom or a monovalent hydrocarbon group having 1 to 10 carbon atoms, or taken together represent a divalent cyclic hydrocarbon group having 3 to 20 carbon atoms together with the carbon atoms to which $R^5$ and $R^6$ are bonded;

$R^7$ and $R^8$ each independently represent a hydrogen atom or a monovalent hydrocarbon group having 1 to 10 carbon atoms, or taken together represent a divalent cyclic hydrocarbon group having 3 to 20 carbon atoms together with the carbon atoms to which $R^7$ and $R^8$ are bonded;

$R^9$ and $R^{10}$ each independently represent a monovalent organic group having 1 to 10 carbon atoms, or taken together represent a 3- to 30-membered divalent cyclic organic group together with the carbon atom to which $R^9$ and $R^{10}$ are bonded;

n1 is an integer of 1 to 4, and when n1 is 2 or more, a plurality of $R^5$ are the same or different from each other, and a plurality of $R^6$ are the same or different from each other; and n2 is an integer of 0 to 3, and when n2 is 2 or more, a plurality of $R^7$ are the same or different from each other, and a plurality of $R^8$ are the same or different from each other.

2. The radiation-sensitive resin composition according to claim 1, further comprising a photodegradable base.

3. The radiation-sensitive resin composition according to claim 1, wherein the resin further comprises a structural unit represented by formula (2):

(2)

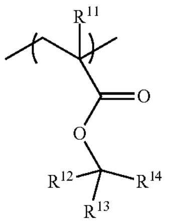

wherein in formula (2), $R^{11}$ is a hydrogen atom, a fluorine atom, a methyl group, or a trifluoromethyl group;

$R^{12}$ is a monovalent hydrocarbon group having 1 to 20 carbon atoms; and $R^{13}$ and $R^{14}$ each independently are a monovalent chain hydrocarbon group having 1 to 10 carbon atoms or a monovalent alicyclic hydrocarbon group having 3 to 20 carbon atoms, or taken together represent a divalent alicyclic hydrocarbon group having 3 to 20 carbon atoms together with the carbon atom to which $R^{13}$ and $R^{14}$ are bonded.

4. The radiation-sensitive resin composition according to claim 1, wherein the resin further comprises a structural unit comprising at least one structure selected from the group consisting of a lactone structure, a cyclic carbonate structure, and a sultone structure.

5. The radiation-sensitive resin composition according to claim 1, wherein n1 is 1 or 2, and n2 is 0 or 1.

6. The radiation-sensitive resin composition according to claim 1, wherein a content of the structural unit represented by the formula (1) in the resin is 1 to 50 mol % relative to a total molar amount of structural units constituting the resin.

7. A method for forming a resist pattern, the method comprising:

directly or indirectly applying the radiation-sensitive resin composition according to claim 1 to a substrate to form a resist film;

exposing the resist film to light; and developing the exposed resist film.

8. The method according to claim 7, wherein the resist film is exposed to an extreme ultraviolet ray (EUV), an X-ray, or an electron beam (EB).

9. The method according to claim 7, wherein the exposed resist film is developed with an organic solvent so that a negative tone pattern is formed.

10. The method according to claim 7, wherein the exposed resist film is developed with an alkaline developer so that a positive tone pattern is formed.

11. The method according to claim 7, wherein the radiation-sensitive resin composition further comprises a photodegradable base.

12. The method according to claim 7, wherein the resin further comprises a structural unit represented by formula (2):

(2)

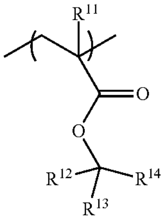

wherein in formula (2), $R^{11}$ is a hydrogen atom, a fluorine atom, a methyl group, or a trifluoromethyl group;

$R^{12}$ is a monovalent hydrocarbon group having 1 to 20 carbon atoms; and $R^{13}$ and $R^{14}$ each independently are a monovalent chain hydrocarbon group having 1 to 10 carbon atoms or a monovalent alicyclic hydrocarbon group having 3 to 20 carbon atoms, or taken together represent a divalent alicyclic hydrocarbon group having 3 to 20 carbon atoms together with the carbon atom to which $R^{13}$ and $R^{14}$ are bonded.

13. The method according to claim 7, wherein the resin further comprises a structural unit comprising at least one structure selected from the group consisting of a lactone structure, a cyclic carbonate structure, and a sultone structure.

14. A polymer comprising a structural unit represented by formula (1):

(1)

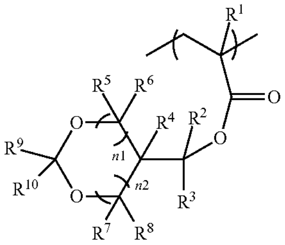

wherein in formula (1), $R^1$ is a hydrogen atom, a fluorine atom, a methyl group, or a trifluoromethyl group;

$R^2$ and $R^3$ each independently represent a monovalent hydrocarbon group having 1 to 10 carbon atoms, or taken together represent a divalent cyclic hydrocarbon group having 3 to 20 carbon atoms together with the carbon atom to which $R^2$ and $R^3$ are bonded;

$R^4$ is a hydrogen atom or a monovalent hydrocarbon group having 1 to 10 carbon atoms;

$R^5$ and $R^6$ each independently represent a hydrogen atom or a monovalent hydrocarbon group having 1 to 10 carbon atoms, or taken together represent a divalent cyclic hydrocarbon group having 3 to 20 carbon atoms together with the carbon atoms to which $R^5$ and $R^6$ are bonded;

$R^7$ and $R^8$ each independently represent a hydrogen atom or a monovalent hydrocarbon group having 1 to 10 carbon atoms, or taken together represent a divalent cyclic hydrocarbon group having 3 to 20 carbon atoms together with the carbon atoms to which $R^7$ and $R^8$ are bonded;

$R^9$ and $R^{10}$ each independently represent a monovalent organic group having 1 to 10 carbon atoms, or taken together represent a 3- to 30-membered divalent cyclic organic group together with the carbon atom to which $R^9$ and $R^{10}$ are bonded;

n1 is an integer of 1 to 4, and when n1 is 2 or more, a plurality of $R^5$ are the same or different from each other, and a plurality of $R^6$ are the same or different from each other; and n2 is an integer of 0 to 3, and when n2 is 2 or more, a plurality of $R^7$ are the same or different from each other, and a plurality of $R^8$ are the same or different from each other.

15. The polymer according to claim 14, further comprising a structural unit represented by formula (2):

(2)

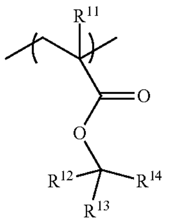

wherein in formula (2), $R^{11}$ is a hydrogen atom, a fluorine atom, a methyl group, or a trifluoromethyl group;

$R^{12}$ is a monovalent hydrocarbon group having 1 to 20 carbon atoms; and $R^{13}$ and $R^{14}$ each independently are a monovalent chain hydrocarbon group having 1 to 10 carbon atoms or a monovalent alicyclic hydrocarbon group having 3 to 20 carbon atoms, or taken together represent a divalent alicyclic hydrocarbon group having 3 to 20 carbon atoms together with the carbon atom to which $R^{13}$ and $R^{14}$ are bonded.

16. The polymer according to claim 14, further comprising a structural unit comprising at least one structure selected from the group consisting of a lactone structure, a cyclic carbonate structure, and a sultone structure.

17. The polymer according to claim 14, wherein n1 is 1 or 2, and n2 is 0 or 1.

18. The polymer according to claim 14, wherein a content of the structural unit represented by the formula (1) in the polymer is 1 to 50 mol % relative to a total molar amount of structural units constituting the polymer.

19. A compound represented by formula (3):

(3)

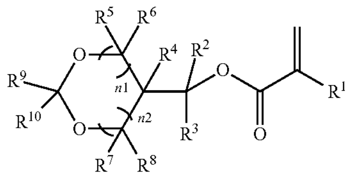

wherein in formula (1), $R^1$ is a hydrogen atom, a fluorine atom, a methyl group, or a trifluoromethyl group;

$R^2$ and $R^3$ each independently represent a monovalent hydrocarbon group having 1 to 10 carbon atoms, or taken together represent or a divalent cyclic hydrocarbon group having 3 to 20 carbon atoms together with the carbon atoms to which $R^2$ and $R^3$ are bonded;

$R^4$ is a hydrogen atom or a monovalent hydrocarbon group having 1 to 10 carbon atoms;

$R^5$ and $R^6$ each independently represent a hydrogen atom or a monovalent hydrocarbon group having 1 to 10 carbon atoms, or taken together represent a divalent cyclic hydrocarbon group having 3 to 20 carbon atoms together with the carbon atoms to which $R^5$ and $R^6$ are bonded;

$R^7$ and $R^8$ each independently represent a hydrogen atom or a monovalent hydrocarbon group having 1 to 10 carbon atoms, or taken together represent a divalent cyclic hydrocarbon group having 3 to 20 carbon atoms together with the carbon atoms to which $R^7$ and $R^8$ are bonded;

$R^9$ and $R^{10}$ each independently represent a monovalent organic group having 1 to 10 carbon atoms, or taken together represent a 3- to 30-membered divalent cyclic organic group together with the carbon atom to which $R^9$ and $R^{10}$ are bonded;

n1 is an integer of 1 to 4, and when n1 is 2 or more, a plurality of $R^5$ are the same or different from each other, and a plurality of $R^6$ are the same or different from each other; and n2 is an integer of 0 to 3, and when n2 is 2 or more, a plurality of $R^7$ are the same or different from each other, and a plurality of $R^8$ are the same or different from each other.

20. The compound according to claim 19, wherein n1 is 1 or 2, and n2 is 0 or 1.

* * * * *